United States Patent [19]
deSolms

[11] Patent Number: 5,869,682
[45] Date of Patent: Feb. 9, 1999

[54] INHIBITORS OF FARNESYL-PROTEIN TRANSFERASE

[75] Inventor: S. Jane deSolms, Norristown, Pa.

[73] Assignee: Merck & Co., Inc., Rahway, N.J.

[21] Appl. No.: 826,291

[22] Filed: Mar. 27, 1997

Related U.S. Application Data

[60] Provisional application No. 60/014,774 Apr. 3, 1996.

[51] Int. Cl.$^6$ ............ C07D 233/61; A61K 31/415
[52] U.S. Cl. .................. 548/335.5; 548/335.1; 548/311.1; 514/397
[58] Field of Search .............. 548/335.1, 311.1, 548/335.5

[56] References Cited

U.S. PATENT DOCUMENTS

| | | | |
|---|---|---|---|
| 4,829,065 | 5/1989 | Pascal et al. | 514/428 |
| 5,159,083 | 10/1992 | Thurkauf et al. | 548/335.5 |
| 5,439,918 | 8/1995 | deSolms et al. | 514/307 |
| 5,491,164 | 2/1996 | deSolms et al. | 514/423 |
| 5,571,835 | 11/1996 | Anthony et al. | 514/255 |
| 5,576,313 | 11/1996 | Fisher et al. | 514/211 |
| 5,627,202 | 5/1997 | deSolms | 514/397 |

FOREIGN PATENT DOCUMENTS

| | | |
|---|---|---|
| WO 96/30343 | 10/1996 | WIPO . |
| WO 96/37204 | 11/1996 | WIPO . |

OTHER PUBLICATIONS

Exp. Opin. Ther. Patents, vol. 5(12), pp. 1269–1271 (1995), by S. L. Graham.
J. of Biol. Chem., vol. 268, No. 11, pp. 7617–7620 (1993), by J. B. Gibbs, et al.
J. of Biol. Chem., vol. 269, No. 44, pp. 27706–27714 (1994), by G. L. James, et al.
J. of Biol. Chem., vol. 270, No. 11, pp. 6221–6226 (1995), by G. L. James, et al.
Science, vol. 260, pp. 1934–1937 (1993), by N. E. Kohl, et al.
Proc. Natl. Acad. Sci. USA, vol. 91, pp. 9141–9145 (1994), by N. E. Kohl, et al.
Nature Medicine, vol. 1, No. 8, pp. 792–797 (1995), by N. E. Kohl, et al.
Cancer Research, vol. 55, pp. 5302–5309 (1995), by L. Sepp–Lorenzino, et al.

*Primary Examiner*—Johann Richter
*Assistant Examiner*—Ebenezer Sackey
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

21 Claims, No Drawings

5,869,682

INHIBITORS OF FARNESYL-PROTEIN TRANSFERASE

Provisioned application of 60/014,774 filed on Apr. 3,1996

BACKGROUND OF THE INVENTION

The Ras proteins (Ha-Ras, Ki4a-Ras, Ki4b-Ras and N-Ras) are part of a signaling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises analogs of the CA$^1$A$^2$X motif of the protein Ras that is modified by farnesylation in vivo. These CA$^1$A$^2$X analogs inhibit the farnesylprotein transferase. Furthermore, these CA$^1$A$^2$X analogs differ from those previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. The compounds of the instant invention also incorporate a cyclic amine moiety in the $A^2$ position of the motif. The compounds of the instant invention also do not contain a carboxylic acid, and therefore do not require a prodrug ester for improved cell permeability. Further contained in this invention are chemotherapeutic compositions containing these farnesyl transferase inhibitors and methods for their production.

The compounds of this invention are illustrated by the formulae:

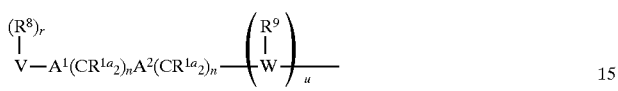

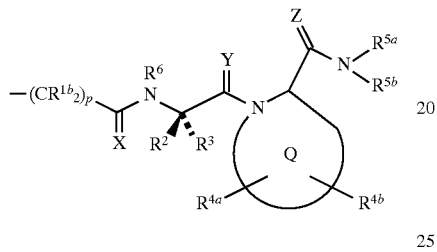

DETAILED DESCRIPTION OF THE INVENTION

The compounds of this invention inhibit the farnesyl-protein transferase. In a first embodiment of this invention, the farnesyl-protein transferase inhibitors are illustrated by the formula I:

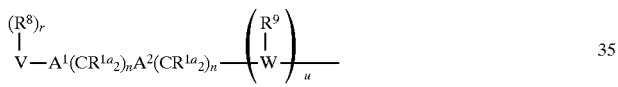

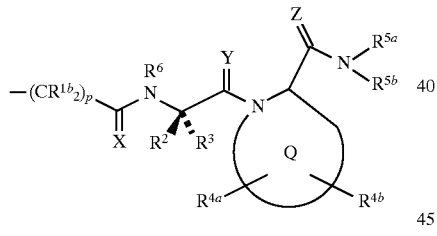

wherein:
$R^{1a}$ and $R^{1b}$ are independently selected from:
a) hydrogen,
b) aryl, heterocycle, cycloalkyl, alkenyl, alkynyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $CON(R^{10})_2-$, $N_3$, $-N(R^{10})_2$, or $R^{11}OC(O)NR^{10}-$,
c) $C_1-C_6$ alkyl unsubstituted or substituted by aryl, heterocyclic, cycloalkyl, alkenyl, alkynyl, $R^{10}O-$, $R^{11}S(O)_m-$, $R^{10}C(O)NR^{10}-$, CN, $(R^{10})_2N-C(NR^{10})-$, $R^{10}C(O)-$, $CON(R^{10})_2-$, $N_3$, $-N(R^{10})_2$, or $R^{11}OC(O)-NR^{10}-$;

$R^2$ and $R^3$ are independently selected from:
a) a side chain of a naturally occurring amino acid,
b) an oxidized form of a side chain of a naturally occurring amino acid which is:
i) methionine sulfoxide, or
ii) methionine sulfone, and
c) substituted or unsubstituted $C_1-C_{20}$ alkyl, $C_2-C_{20}$ alkenyl, $C_3-C_{10}$ cycloalkyl, aryl or heterocyclic group, wherein the substituent is selected from F, Cl, Br, $N(R^{10})_2$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $CON(R^{10})_2-$, $N_3$, $-N(R^{10})_2$, $R^{11}OC(O)NR^{10}-$ and $C_1-C_{20}$ alkyl, and
d) $C_1-C_6$ alkyl substituted with an unsubstituted or substituted group selected from aryl, heterocycle and $C_3-C_{10}$ cycloalkyl; or
$R^2$ and $R^3$ are combined to form $-(CH_2)_s-$; or
$R^2$ or $R^3$ are combined with $R^6$ to form a ring such that

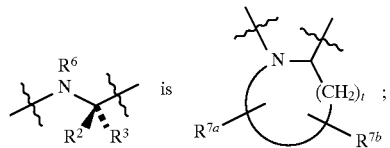

$R^{4a}$, $R^{4b}$, $R^{7a}$ and $R^{7b}$ are independently selected from:
a) hydrogen,
b) $C_1-C_6$ alkyl unsubstituted or substituted by alkenyl, $R^{10}O-$, $R^{11}S(O)_m-$, $R^{10}C(O)NR^{10}-$, CN, $N_3$, $(R^{10})_2N-C(NR^{10})-$, $R^{10}C(O)-$, $CON(R^{10})_2-$, $-N(R^{10})_2$, or $R^{11}OC(O)NR^{10}-$,
c) aryl, heterocycle, cycloalkyl, alkenyl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $CON(R^{10})_2-$, $N_3$, $-N(R^{10})_2$, or $R^{11}OC(O)NR^{10}-$, and
d) $C_1-C_6$ alkyl substituted with an unsubstituted or substituted group selected from aryl, heterocyclic and $C_3-C_{10}$ cycloalkyl;

$R^{5a}$ and $R^{5b}$ are independently selected from:
a) hydrogen,
b) substituted or unsubstituted $C_1-C_{20}$ alkyl, $C_2-C_{20}$ alkenyl, $C_3-C_{10}$ cycloalkyl, aryl or heterocycle group,
wherein the substituent is selected from F, Cl, Br, $(R^{10})_2NC(O)-$, $NO_2$, $R^{10}O-$, $R^{11}S(O)_m-$, $R^{10}C(O)NR^{10}-$, CN, $(R^{10})_2N-C(NR^{10})-$, $R^{10}C(O)-$, $CON(R^{10})_2-$, $N_3$, $-N(R^{10})_2$, $R^{11}OC(O)NR^{10}-$ and $C_1-C_{20}$ alkyl,
d) $C_1-C_6$ alkyl substituted with an unsubstituted or substituted group selected from aryl, heterocycle and $C_3-C_{10}$ cycloalkyl; or
$R^{5a}$ and $R^{5b}$ are combined to form $-(CH_2)_s-$ wherein one of the carbon atoms is optionally replaced by a moiety selected from: O, $S(O)_m$, $-NC(O)-$, and $-N(COR^{10})-$;

$R^6$ is independently selected from hydrogen or $C_1-C_6$ alkyl;

$R^8$ is independently selected from:
a) hydrogen,
b) aryl, heterocycle, cycloalkyl, alkenyl, alkynyl, perfluoroalkyl, F, Cl, Br, $R^{10}O-$, $R^{11}S(O)_m-$, $R^{10}C(O)NR^{10}-$, CN, $NO_2$, $R^{10}_2N-C(NR^{10})-$, $R^{10}C(O)-$, $CON(R^{10})_2-$, $N_3$, $-N(R^{10})_2$, or $R^{11}OC(O)NR^{10}-$, and
c) $C_1-C_6$ alkyl unsubstituted or substituted by aryl, heterocycle, cycloalkyl, alkenyl, alkynyl, perfluoroalkyl, F, Cl, Br, $R^{10}O-$, $R^{11}S(O)_m-$, $R^{10}C(O)NH-$, CN, $H_2N-C(NH)-$, $R^{10}C(O)-$, $CON(R^{10})_2-$, $N_3$, $-N(R^{10})_2$, or $CON(R^{10})_2NH-$;

$R^9$ is selected from:
a) hydrogen,
b) alkenyl, alkynyl, perfluoroalkyl, F, Cl, Br, $R^{10}O-$, $R^{11}S(O)_m-$, $R^{10}C(O)NR^{10}-$, CN, $NO_2$, $(R^{10})_2N-$ C—(NR$^{10}$)—, R$^{10}$C(O)—, CON(R$^{10}$)$_2$—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, CON(R$^{10}$)$_2$—, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

Q is a substituted or unsubstituted nitrogen-containing C$_4$–C$_9$ mono or bicyclic ring system, wherein the non-nitrogen containing ring may be a C$_5$–C$_7$ saturated ring;

V is selected from:
 a) hydrogen,
 b) heterocycle,
 c) aryl,
 d) C$_1$–C$_{20}$ alkyl wherein from 0 to 4 carbon atoms are replaced with a heteroatom selected from O, S, and N, and
 e) C$_2$–C$_{20}$ alkenyl,
provided that V is not hydrogen if A$^1$ is S(O)$_m$ and V is not hydrogen if A$^1$ is a bond, n is 0 and A$^2$ is (O)$_m$;

W is a heterocycle;

X, Y and Z are independently H$_2$ or 0;

m is 0, 1 or 2;

n is 0, 1, 2, 3 or 4;

p is 0, 1, 2, 3 or 4;

r is 0 to 5, provided that r is 0 when V is hydrogen;

s is 4 or 5;

t is 3, 4 or 5; and u is 0 or 1;

or the pharmaceutically acceptable salts, crystal forms, hydrates and isomers thereof.

In a more preferred embodiment of this invention, the Ras farnesyl transferase inhibitors are illustrated by the Formula I:

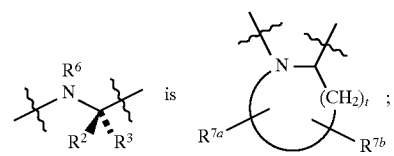

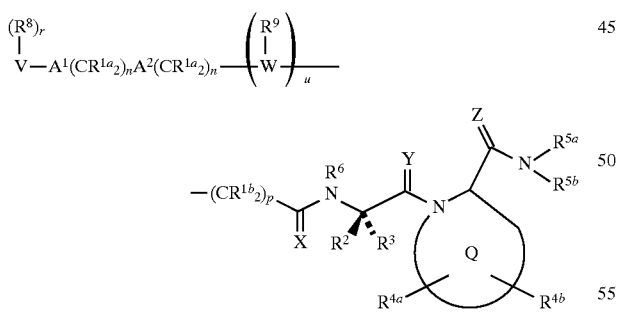

wherein:
 R$^{1a}$ is independently selected from: hydrogen or C$_1$–C$_6$ alkyl;
 R$^{1b}$ is independently selected from:
  a) hydrogen,
  b) aryl, heterocycle, cycloalkyl, R$^{10}$O—, —N(R$^{10}$)$_2$ or alkenyl,
  c) C$_1$–C$_6$ alkyl unsubstituted or substituted by aryl, heterocycle, cycloalkyl, alkenyl, R$^{10}$O—, or —N(R$^{10}$)$_2$;

R$^2$ and R$^3$ are independently selected from:
 a) a side chain of a naturally occurring amino acid,
 b) an oxidized form of a side chain of a naturally occurring amino acid which is:
  i) methionine sulfoxide, or
  ii) methionine sulfone,
 c) substituted or unsubstituted C$_1$–C$_{10}$ alkyl, C$_2$–C$_{10}$ alkenyl, C$_3$–C$_{10}$ cycloalkyl, aryl or heterocyclic group,
  wherein the substituent is selected from F, Cl, Br, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, CON(R$^{10}$)$_2$—, N$_3$, —N(R$^{10}$)$_2$, R$^{11}$OC(O)NR$^{10}$- and C$_1$–C$_{20}$ alkyl, and
 d) C$_1$–C$_6$ alkyl substituted with an unsubstituted or substituted group selected from aryl, heterocycle and C$_3$–C$_{10}$ cycloalkyl; or R$^2$ and R$^3$ are combined to form —(CH$_2$)$_s$—; or R$^2$ or R$^3$ are combined with R$^6$ to form a ring such that R$^{4a}$ and R$^{7a}$ are independently selected from:
 a) hydrogen,
 b) C$_1$–C$_6$ alkyl unsubstituted or substituted by alkenyl, R$^{10}$O—, R$^{11}$S(O)$_m$—, R$^{10}$C(O)NR$^{10}$—, CN, N$_3$, (R$^{10}$)$_2$N—C(NR$^{10}$)—, R$^{10}$C(O)—, CON(R$^{10}$)$_2$—, —N(R$^{10}$)$_2$, or R$^{11}$OC(O)NR$^{10}$—,
 c) aryl, heterocycle, cycloalkyl, alkenyl, R$^{10}$O—, R$^{11}$S(O)$_m$—, R$^{10}$C(O)NR$^{10}$—, CN, NO$_2$, (R$^{10}$)$_2$N—C(NR$^{10}$)—, R$^{10}$C(O)—, CON(R$^{10}$)$_2$—N$_3$, —N(R$^{10}$)$_2$, or R$^{11}$OC(O)NR$^{10}$—, and
 d) C$_1$–C$_6$ alkyl substituted with an unsubstituted or substituted group selected from aryl, heterocyclic and C$_3$–C$_{10}$ cycloalkyl;

R$^{4b}$ and R$^{7b}$ are hydrogen;

R$^{5a}$ is selected from:
 a) substituted or unsubstituted C$_1$–C$_{10}$ alkyl, C$_2$–C$_{10}$ alkenyl, C$_3$–C$_{10}$ cycloalkyl, aryl or heterocyclic group,
  wherein the substituent is selected from F, Cl, Br, NO$_2$, R$^{10}$—, R$^{11}$S(O)$_m$—, R$^{10}$C(O)NR$^{10}$—, (R$^{10}$)$_2$NC(O)—, CN, (R$^{10}$)$_2$N—C(NR$^{10}$)—, R$^{10}$C(O)—, CON(R$^{10}$)$_2$—, N$_3$, —N(R$^{10}$)$_2$, R$^{11}$OC(O)NR$^{10}$— and C$_1$–C$_{20}$ alkyl, and
 b) C$_1$–C$_6$ alkyl substituted with an unsubstituted or substituted group selected from aryl, heterocycle and C$_3$–C$_{10}$ cycloalkyl;

R$^{5b}$ is selected from:
 a) hydrogen, and
 b) C$_1$–C$_3$ alkyl;

R$^6$ is independently selected from hydrogen or C$_1$–C$_6$ alkyl;

R$^8$ is independently selected from:
 a) hydrogen,
 b) C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, CON(R$^{10}$)$_2$—, —N(R$^{10}$)$_2$, or R$^{11}$OC(O)NR$^{10}$—, and
 c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, CON(R$^{10}$)$_2$—, —N(R$^{10}$)$_2$, or R$^{11}$OC(O)NR$^{10}$—;

$R^9$ is selected from:
 a) hydrogen,
 b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $CON(R^{10})_2$—, —$N(R^{10})_2$, or $R^{11}OC(O)NR^{10}$—, and

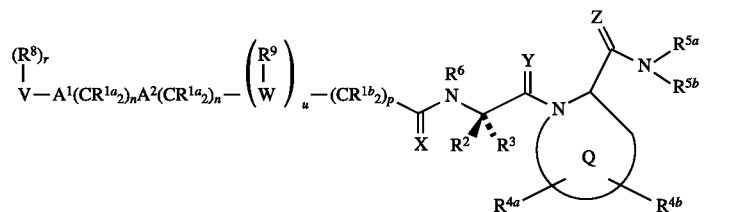

c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $CON(R^{10})_2$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

Q is selected from:

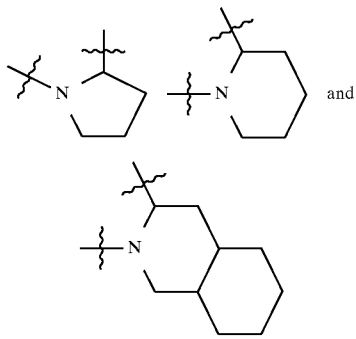

$A^1$ and $A^2$ are independently selected from: a bond, —CH=CH—, —C≡C—, —C(O)—, —C(O)$NR^{10}$—, O, —$N(R^{10})$—, or $S(O)_m$;

V is selected from:
 a) hydrogen,
 b) heterocycle selected from pyrrolidinyl, imidazolyl, pyridinyl, thiazolyl, pyridonyl, 2-oxopiperidinyl, indolyl, quinolinyl, isoquinolinyl, and thienyl,
 c) aryl,
 d) $C_1$–$C_{20}$ alkyl wherein from 0 to 4 carbon atoms are replaced with a heteroatom selected from O, S, and N, and
 e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

X, Y and Z are independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

t is 3, 4 or 5; and u is 0 or 1;

or the pharmaceutically acceptable salts, hydrates, crystal forms and isomers thereof.

In an even more preferred embodiment of this invention, the Ras farnesyl transferase inhibitors are illustrated by the Formula II:

wherein:
 $R^{1a}$ is independently selected from: hydrogen or $C_1$–$C_6$ alkyl;
 $R^{1b}$ is independently selected from:
  a) hydrogen,
  b) aryl, heterocycle, cycloalkyl, $R^{10}O$—, —$N(R^{10})_2$ or alkenyl,
  c) $C_1$–$C_6$ alkyl unsubstituted or substituted by aryl, heterocycle, cycloalkyl, alkenyl, $R^{10}O$—, or —$N(R^{10})_2$;

$R^2$ or $R^3$ are combined with $R^6$ to form a ring such that

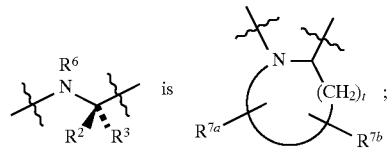

$R^{4a}$ is independently selected from:
 a) hydrogen,
 b) $C_1$–$C_6$ alkyl unsubstituted or substituted by alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $CON(R^{10})_2$—, —$N(R^{10})_2$, or $R^{11}OC(O)NR^{10}$—,
 c) aryl, heterocycle, cycloalkyl, alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $CON(R^{10})_2$—, $N_3$, —$N(R^{10})_2$, or $R^{11}OC(O)NR^{10}$—, and
 d) $C_1$–$C_6$ alkyl substituted with an unsubstituted or substituted group selected from aryl, heterocyclic and $C_3$–$C_{10}$ cycloalkyl;

$R^{4b}$ and $R^{7b}$ are hydrogen;

$R^{5a}$ is selected from:
 a) substituted or unsubstituted $C_1$–$C_{10}$ alkyl, $C_2$–$C_{10}$ alkenyl, $C_3$–$C_{10}$ cycloalkyl, aryl or heterocyclic group,
  wherein the substituent is selected from F, Cl, Br, $NO_2$, $R^{10}O$—, $R^{11}S(O)_m$—, $R^{10}C(O)NR^{10}$—, $(R^{10})_2NC(O)$—, CN, $(R^{10})_2N$—$C(NR^{10})$—, $R^{10}C(O)$—, $CON(R^{10})_2$—, $N_3$, —$N(R^{10})_2$, $R^{11}OC(O)NR^{10}$— and $C_1$–$C_{20}$ alkyl, and
 b) $C_1$–$C_6$ alkyl substituted with an unsubstituted or substituted group selected from aryl, heterocycle and $C_3$–$C_{10}$ cycloalkyl;

$R^{5b}$ is selected from:
 a) hydrogen, and
 b) $C_1$–$C_3$ alkyl;

$R^6$ is independently selected from hydrogen or $C_1$–$C_6$ alkyl;

$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $CON(R^{10})_2$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $CON(R^{10})_2$—, —$N(R^{10})_2$, or $R^{11}OC(O)NR^{10}$—;

$R^9$ is selected from:
  a) hydrogen,
  b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $CON(R^{10})_2$—, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $CON(R^{10})_2$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

Q is selected from:

and $A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

X, Y and Z are independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

t is 3, 4 or 5; and u is 0 or 1;

or the pharmaceutically acceptable salts, hydrates, crystal forms or isomers thereof.

In yet a more preferred embodiment of this invention, the Ras farnesyl transferase inhibitors are illustrated by the Formula IV:

wherein:

$R^{1a}$ is independently selected from: hydrogen or $C_1$–$C_6$ alkyl;

$R^{1b}$ is independently selected from:
  a) hydrogen,
  b) aryl, heterocycle, cycloalkyl, $R^{10}O$—, —$N(R^{10})_2$ or alkenyl,
  c) $C_1$–$C_6$ alkyl unsubstituted or substituted by aryl, heterocycle, cycloalkyl, alkenyl, $R^{10}O$—, or —$N(R^{10})_2$;

$R^{4a}$ and $R^{7a}$ are independently selected from:
  a) hydrogen,
  b) $C_1$–$C_6$ alkyl unsubstituted or substituted by alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $CON(R^{10})_2$—, —$N(R^{10})_2$, or $R^{11}OC(O)NR^{10}$—,
  c) aryl, heterocycle, cycloalkyl, alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $CON(R^{10})_2$—, $N_3$, —$N(R^{10})_2$, or $R^{11}OC(O)NR^{10}$—, and
  d) $C_1$–$C_6$ alkyl substituted with an unsubstituted or substituted group selected from aryl, heterocyclic and $C_3$–$C_{10}$ cycloalkyl;

$R^{4b}$ is hydrogen;

$R^{5a}$ is selected from:
  a) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^{10}O$—, $R^{11}S(O)_m$—, $R^{10}C(O)NR^{10}$—, $(R^{10})_2NC(O)$—, CN, $(R^{10})_2N$—$C(NR^{10})$—, $R^{10}C(O)$—, $CON(R^{10})_2$—, $N_3$, —$N(R^{10})_2$, $R^{11}OC(O)NR^{10}$— and $C_1$–$C_{20}$ alkyl, and
  b) $C_1$–$C_6$ alkyl substituted with an unsubstituted or substituted group selected from aryl, heterocycle and $C_3$–$C_{10}$ cycloalkyl;

$R^{5b}$ is selected from:
  a) hydrogen, and
  b) $C_1$–$C_3$ alkyl;
$R^8$ is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $CON(R^{10})_2$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}$—, $R^{10}C(O)NR^{10}$—, $(R^{10})_2N$—$C(NR^{10})$—, $R^{10}C(O)$—, $CON(R^{10})_2$—, —$N(R^{10})_2$, or $R^{11}OC(O)NR^{10}$—;
$R^9$ is selected from:
  a) hydrogen,
  b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $CON(R^{10})_2$—, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $CON(R^{10})_2$—, —$N(R^{10})_2$, or $R^{11}OC(O)NR^{10}$—;
$R^{10}$ is independently selected from hydrogen, $C_1$–$C_6$ alkyl, benzyl and aryl;
$R^{11}$ is independently selected from $C_1$–$C_6$ alkyl and aryl;
Q is selected from:

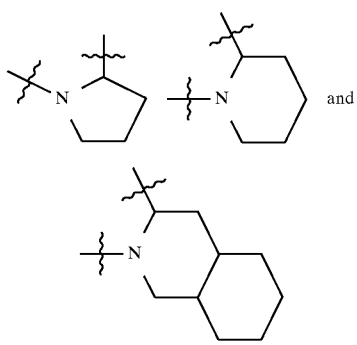

$A^1$ and $A^2$ are independently selected from: a bond, —CH=CH—, —C≡C—, —C(O)—, —C(O)NR$^{10}$—, O, —N(R$^{10}$)—, or S(O)$_m$;
V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

t is 3, 4 or 5; and u is 0 or 1;

or the pharmaceutically acceptable salts, hydrates, crystal forms, or isomers thereof.

In the most preferred embodiment of this invention, the Ras farnesyl transferase inhibitors are illustrated by the Formula V:

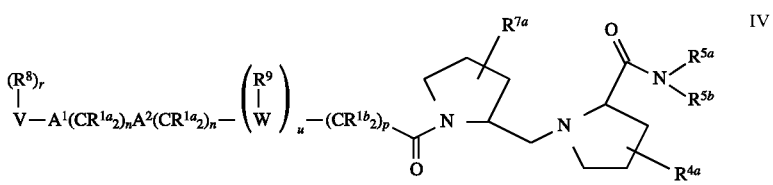

wherein:

$R^{1a}$ is independently selected from: hydrogen or $C_1$–$C_6$ alkyl;

$R^{1b}$ is independently selected from:
  a) hydrogen,
  b) aryl, heterocycle, cycloalkyl, $R^{10}O$—, —$N(R^{10})_2$ or alkenyl,
  c) $C_1$–$C_6$ alkyl unsubstituted or substituted by aryl, heterocycle, cycloalkyl, alkenyl, $R^{10}O$—, or —$N(R^{10})_2$;

$R^{4a}$ and $R^{7a}$ are independently selected from:
  a) hydrogen,
  b) $C_1$–$C_6$ alkyl unsubstituted or substituted by alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, $CON(R^{10})_2$—, —$N(R^{10})_2$, or $R^{11}OC(O)NR^{10}$—,
  c) aryl, heterocycle, cycloalkyl, alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $CON(R^{10})_2$—, $N_3$, —$N(R^{10})_2$, or $R^{11}OC(O)NR^{10}$—, and
  d) $C_1$–$C_6$ alkyl substituted with an unsubstituted or substituted group selected from aryl, heterocyclic and $C_3$–$C_{10}$ cycloalkyl;

$R^{5a}$ is selected from:
  a) substituted or unsubstituted $C_1$–$C_{10}$ alkyl, $C_2$–$C_{10}$ alkenyl, $C_3$–$C_{10}$ cycloalkyl, aryl or heterocyclic group,
    wherein the substituent is selected from F, Cl, Br, $NO_2$, $R^{10}O$—, $R^{11}S(O)_m$—, $R^{10}C(O)NR^{10}$—, $(R^{10})_2NC(O)$—, CN, $(R^{10})_2N$—$C(NR^{10})$—, $R^{10}C(O)$—, $CON(R^{10})_2$—, $N_3$, —$N(R^{10})_2$, $R^{11}OC(O)NR^{10}$— and $C_1$–$C_{20}$ alkyl, and
  b) $C_1$–$C_6$ alkyl substituted with an unsubstituted or substituted group selected from aryl, heterocycle and $C_3$–$C_{10}$ cycloalkyl;

$R^{5b}$ is selected from:
  a) hydrogen, and
  b) $C_1$–$C_3$ alkyl;

R[8] is independently selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{11}C(O)$—, $CON(R^{10})_2$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $CON(R^{10})_2$—, —$N(R^{10})_2$, or $R^{11}OC(O)NR^{10}$—;

R[9] is selected from:
  a) hydrogen,
  b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{11}C(O)$—, $CON(R^{10})_2$—, —$N(R^{10})_2$, or $R^{11}OC(O)NR^{10}$—, and
  c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $CON(R^{10})_2$—, —$N(R^{10})_2$, or $R^{11}OC(O)NR^{10}$—;

R[10] is independently selected from hydrogen, $C_1$–$C_6$ alkyl, benzyl and aryl;
R[11] is independently selected from $C_1$–$C_6$ alkyl and aryl;
A[1] and A[2] are independently selected from: a bond, —CH=CH—, —C≡C—, —C(O)—, —C(O)NR[10]—, O, —N(R[10])—, or $S(O)_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if A[1] is $S(O)_m$ and V is not hydrogen if A[1] is a bond, n is 0 and A[2] is $S(O)_m$;

W is a heterocycle selected from pyrrolidinyl, imidazolyl, pyridinyl, thiazolyl, pyridonyl, 2-oxopiperidinyl, indolyl, quinolinyl, or isoquinolinyl;
  m is 0, 1 or 2;
  n is 0, 1, 2, 3 or 4;
  p is 0, 1, 2, 3 or 4;
  r is 0 to 5, provided that r is 0 when V is hydrogen;
  t is 3, 4 or 5; and
  u is 0 or 1;

or the pharmaceutically acceptable salts, hydrates, crystal forms or isomers thereof.

Examples of the compounds of this invention are as follows:

N-[1-[1-(4-Cyanobenzyl)-1H-imidazol-5-ylacetyl] pyrrolidin-2(S)-ylmethyl]-3(S)-ethyl-proline N-(3-chlorophenylmethyl)-amide N-[1-[1-(4-Cyanobenzyl)-1H-imidazol-5-ylacetyl] pyrrolidin-2(S)-ylmethyl]-3(S)-ethyl-proline N-methyl-N-(3-chlorophenylmethyl)-amide N-[1-[1-(4-Cyanobenzyl)-1H-imidazol-5-ylacetyl]-3(S)-ethylpyrrolidin-2(S)-ylmethyl]-3(S)-ethyl-proline N-(3-chlorophenylmethyl)-amide N-[1-[1-(4-Cyanobenzyl)-1H-imidazol-5-ylacetyl]-3(S)-ethylpyrrolidin-2(S)-ylmethyl]-3(S)-ethyl-proline N-methyl-N-(3-chlorophenylmethyl)-amide N-[1-(3-[1H-Imidazol-4-yl]propionyl)-pyrrolidin-2(S)-ylmethyl]-3(S)-ethyl-proline-N-methyl-N-(3-chlorophenylmethyl) amide N-[1-(3-[1H-Imidazol-4-yl]propionyl)-3(S)-ethylpyrrolidin-2(S)-ylmethyl]-3(S)-ethyl-proline-N-methyl-N-(3-chlorophenylmethyl) amide N-[1-(1-(1-Farnesyl)-1H-imidazol-5-ylacetyl)-pyrrolidin-2(S)-ylmethyl]-3(S)-ethyl-proline-N-methyl-N-(3-chlorophenylmethyl) amide N-[1-(1-(1-Geranyl)-1H-imidazol-5-ylacetyl)-pyrrolidin-2(S)-ylmethyl]-3(S)-ethyl-proline-N-methyl-N-(3-chlorophenylmethyl) amide N-[1-[1-(4-Methoxybenzyl)-1H-imidazol-5-ylacetyl] pyrrolidin-2(S)-ylmethyl]-3(S)-ethyl-proline-N-(3-chlorophenylmethyl) amide N-[1-[1-(4-Methoxybenzyl)-1H-imidazol-5-ylacetyl] pyrrolidin-2(S)-ylmethyl]-3(S)-ethyl-proline-N-methyl-N-(3-chlorophenylmethyl) amide N-[1-[1-(2-Naphthylmethyl)-1H-imidazol-5-ylacetyl] pyrrolidin-2(S)-ylmethyl]-3(S)-ethyl-proline-N-(3-chlorophenylmethyl) amide N-[1-[1-(2-Naphthylmethyl)-1H-imidazol-5-ylacetyl] pyrrolidin-2(S)-ylmethyl]-3(S)-ethyl-proline-N-methyl-N-(3-chlorophenylmethyl) amide or the pharmaceutically acceptable salts thereof.

Specific examples of compounds of the invention are:

N-[1-(3-[1H-Imidazol-4-yl]propionyl)-pyrrolidin-2(S)-ylmethyl]-3(S)-ethyl-proline-N-methyl-N-(3-chlorophenylmethyl) amide

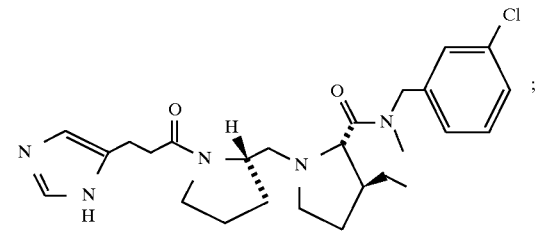

N-[1-[1-(4-Cyanobenzyl)-1H-imidazol-5-ylacetyl] pyrrolidin-2(S)-ylmethyl]-3(S)-ethyl-proline N-(3-chlorophenylmethyl)-amide

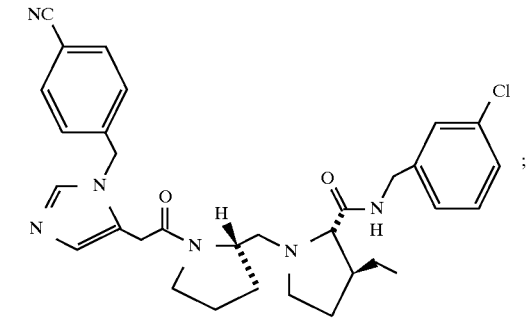

N-[1-[1-(4-Cyanobenzyl)-1H-imidazol-5-ylacetyl] pyrrolidin-2(S)-ylmethyl]-3(S)-ethyl-proline N-methyl-N-(3-chlorophenylmethyl)-amide

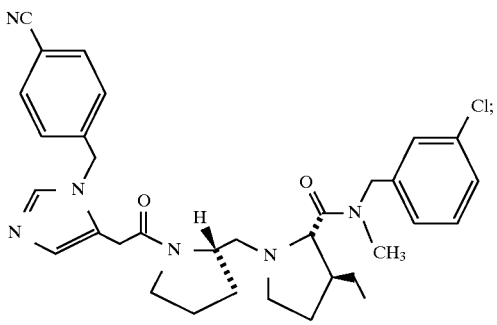

or the pharmaceutically acceptable salts thereof.

In the present invention, the amino acids which are disclosed are identified both by conventional 3 letter and single letter abbreviations as indicated below:

| | | |
|---|---|---|
| Alanine | Ala | A |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1–C_6 \text{ alkyl})_2$, $NO_2$, CN, $(C_1–C_6 \text{ alkyl})O$—, —OH, $(C_1–C_6 \text{ alkyl}) S(O)_m$—, $(C_1–C_6 \text{ alkyl})C(O)NH$—, $H_2N$—C(NH)—, $(C_1–C_6 \text{ alkyl})C(O)$—, $(C_1–C_6 \text{ alkyl})OC(O)$—, $N_3$, $(C_1–C_6 \text{ alkyl})OC(O)NH$— and $C_1–C_{20}$ alkyl.

The following structure:

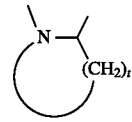

represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

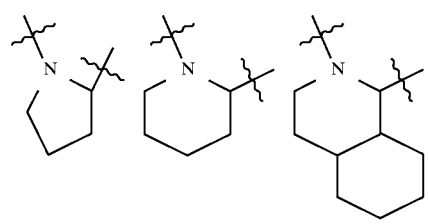

It is also understood that substitution on the cyclic amine moiety by $R^{8a}$ and $R^{8b}$ may be on different carbon atoms or on the same carbon atom.

When $R^3$ and $R^4$ are combined to form —$(CH_2)_s$—, cyclic moieties are formed. Examples of such cyclic moieties include, but are not limited to:

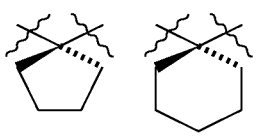

As used herein, the phrase "nitrogen containing $C_4$–$C_9$ mono or bicyclic ring system wherein the non-nitrogen containing ring may be a $C_5$–$C_7$ saturated ring" which defines moiety "Q" of the instant invention includes but is not limited to the following ring systems:

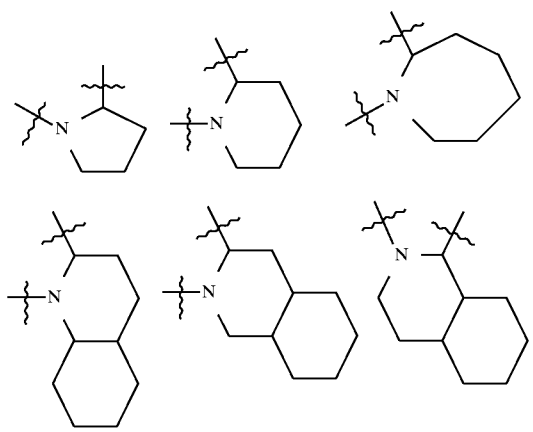

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions els ewhe re in that mole cule. Thus, —$N(R^{10})_2$ represents —NHH, —$NHCH_3$, —$NHC_2H_5$, etc. It is understood that substituents and substitution patterns on the compounds of t he instant invention can be selected by one of ordinary skill in the art to provide compounds that are chemically stable and that can be readily synthesized by techniques known in the art as well as those methods set forth below.

Preferably, $R^{1a}$ and $R^{1b}$ are independently selected from: hydrogen, —$N(R^8)_2$, $R^8C(O)NR^8$— or $C_1$–$C_6$ alkyl unsubstituted or substituted by —$N(R^8)_2$, $R^8O$—or $R^8C(O)NR^8$—.

Preferably, $R^2$ is the sidechain of glycine (hydrogen).
Preferably, $R^3$ is selected from:
a) a side chain of a naturally occurring amino acid,
b) substituted or unsubstituted $C_1$–$C_{20}$ alkyl, wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $CON(R^{10})_2$—, $N_3$, —$N(R^{10})_2$, $R^{11}OC(O)NR^{10}$— and $C_1$–$C_{20}$ alkyl, and
c) $C_1$–$C_6$ alkyl substituted with an unsubstituted or substituted group selected from aryl, heterocycle and $C_3$–$C_{10}$ cycloalkyl; or $R^3$ is combined with $R^6$ to form pyrrolidinyl ring.

Preferably, $R^{4a}$, $R^{4b}$, $R^{7a}$ and $R^{7b}$ are independently selected from: hydrogen, $C_1$–$C_6$ alkyl, aryl and benzyl.

Preferably, $R^{5a}$ and $R^{5b}$ are independently selected from: hydrogen, unsubstituted or substituted $C_1$–$C_6$ alkyl, aryl, or C1–3 alkyl substituted with an unsubstituted or substituted group selected from aryl or heterocycle.

Preferably, $R^6$ is: hydrogen or is combined with $R^3$ to form pyrrolidinyl ring.

Preferably, $R^8$ is selected from: hydrogen, perfluoroalkyl, F, Cl, Br, $R^{10}O$—, $R^{11}S(O)_m$—, CN, $NO_2$, $R^{10}_2N$—$C(NR^{10})$—, $R^{10}C(O)$—, $CON(R^{10})_2$—, $N_3$, —$N(R^{10})_2$, or $R^{11}OC(O)NR^{10}$— and $C_1$–$C_6$ alkyl.

Preferably, $R^9$ is hydrogen.
Preferably, $R^{10}$ is selected from H, $C_1$–$C_6$ alkyl and benzyl.

Preferably, $R^{12}$ is selected from $C_1$–$C_6$ alkyl and benzyl.
Preferably, $A^1$ and $A^2$ are independently selected from: a bond, —$C(O)NR^{10}$—, —$NR^{10}C(O)$—, O, —$N(R^{10})$—, —$S(O)_2N(R^{10})$— and —$N(R^{10})S(O)_2$—.

Preferably, Q is a pyrrolidinyl ring.
Preferably, V is selected from hydrogen, heterocycle and aryl.

Preferably, n, p and r are independently 0, 1, or 2.
Preferably t is 3.

The pharmaceutically acceptable salts of the compounds of this invention can be synthesized from the compounds of this invention which contain a basic moiety conventional chemical methods. Generally, the salts are prepared by ion exchange chromatography or by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "*The Peptides*", Vol. I, Academic Press 1965, or Bodanszky et al., "*Peptide Synthesis*", Interscience Publishers, 1966, or McOmie (ed.) "*Protective Groups in Organic Chemistry*", Plenum Press, 1973, or Barany et al., "*The Peptides: Analysis, Synthesis, Biology*" 2, Chapter 1, Academic Press, 1980, or Stewart et al., "*Solid Phase Peptide Synthesis*", Second Edition, Pierce Chemical Company, 1984. The teachings of these works are hereby incorporated by reference.

Abbreviations used in the description of the chemistry and in the Examples that follow are:
$Ac_2O$ Acetic anhydride;
Boc t-Butoxycarbonyl;
DBU 1,8-diazabicyclo[5.4.0]undec-7-ene;
DMAP 4-Dimethylaminopyridine;
DME 1,2-Dimethoxyethane;
DMF Dimethylformamide;
EDC 1-(3-dimethylaminopropyl)-3-ethyl-carbodiimidehydrochloride;
HOBT 1-Hydroxybenzotriazole hydrate;
$Et_3N$ Triethylamine;
EtOAc Ethyl acetate;
FAB Fast atom bombardment;
HOOBT 3-Hydroxy-1,2,2-benzotriazin-4(3H)-one;
HPLC High-performance liquid chromatography;
MCPBA m-Chloroperoxybenzoic acid;

MsCl Methanesulfonyl chloride;
NaHMDS Sodium bis(trimethylsilyl)amide;
Py Pyridine;
TFA Trifluoroacetic acid;
THF Tetrahydrofuran.

Compounds of this invention are prepared by employing the reactions shown in the following Reaction Schemes A–J, in addition to other standard manipulations such as ester hydrolysis, cleavage of protecting groups, etc., as may be known in the literature or exemplified in the experimental procedures. Some key bond-forming and peptide modifying reactions are:

Reaction A Amide bond formation and protecting group cleavage using standard solution or solid phase methodologies.

Reaction B Preparation of a reduced peptide subunit by reductive alkylation of an amine by an aldehyde using sodium cyanoborohydride or other reducing agents.

Reaction C Deprotection of the reduced peptide subunit

Reaction D Amide bond formation and protecting group cleavage using standard solution or solid phase methodologies.

Reaction E Preparation of a reduced subunit by borane reduction of the amide moiety.

Reaction Schemes A–E illustrate bond-forming and peptide modifying reactions incorporating acyclic peptide units. It is well understood that such reactions are equally useful when the —NHC(RA)— moiety of the reagents and compounds illustrated is replaced with the following moiety:

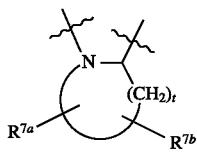

These reactions may be employed in a linear sequence to provide the compounds of the invention or they may be used to synthesize fragments which are subsequently joined by the reactions described in the Reaction Schemes.

REACTION SCHEME A
Reaction A. Coupling of residues to form an amide bond

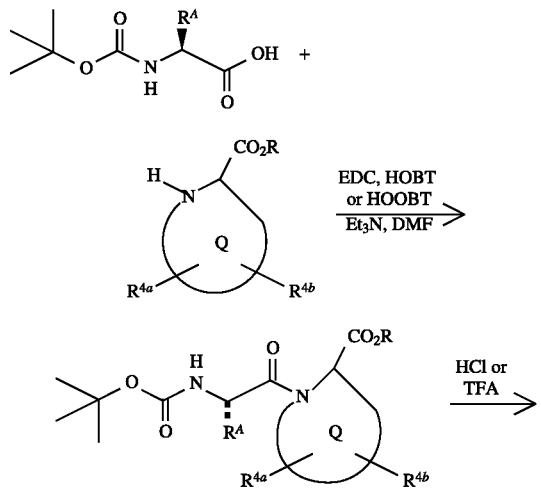

REACTION SCHEME A
Reaction A. Coupling of residues to form an amide bond

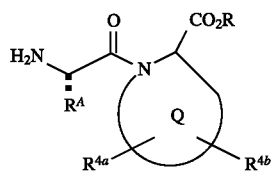

REACTION SCHEME B
Reaction B. Preparation of reduced peptide subunits by reductive alkylation

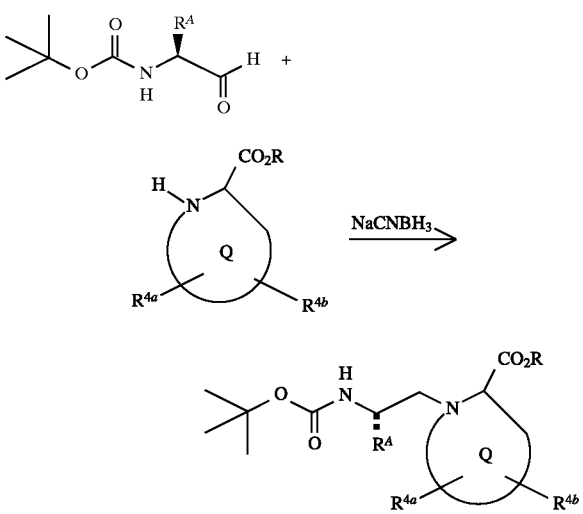

REACTION SCHEME C
Reaction C. Deprotection of reduced peptide subunits

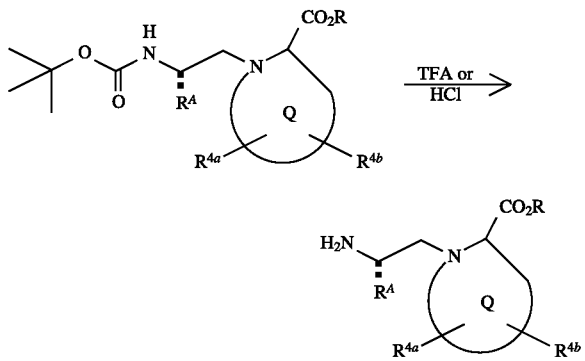

REACTION SCHEME D
Reaction D. Coupling of residues to form an amide bond

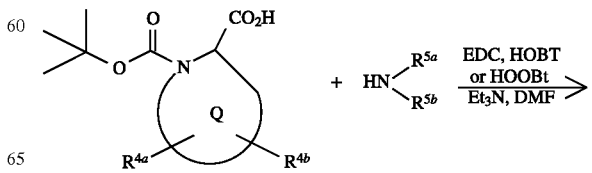

REACTION SCHEME D
Reaction D. Coupling of residues to form an amide bond

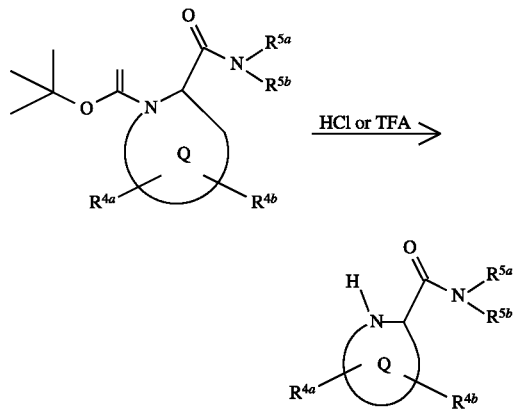

REACTION SCHEME E
Reaction E. Preparation of reduced dipeptides from peptides

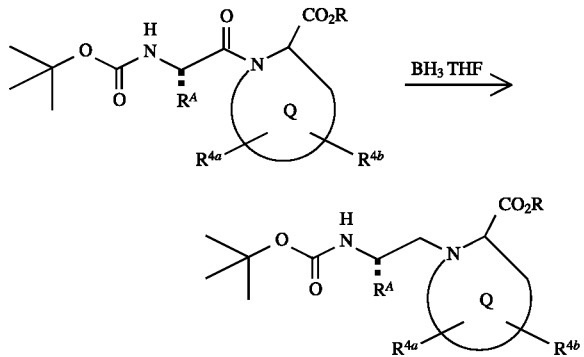

where $R^A$ is $R^2$, $R^3$, $R^{5a}$ or $R^{5b}$ as previously defined; $R^{4a}$ and $R^{4b}$ are as previously defined; and R is an appropriate protecting group for the carboxylic acid.

Reaction Schemes F–M illustrate reactions wherein the non-sulfhydryl-containing moiety at the N-terminus of the compounds of the instant invention is attached to an acyclic peptide unit which may be further elaborated to provide the instant compounds. It is well understood that such reactions are equally useful when the —NHC(RA)— moiety of the reagents and compounds illustrated is replaced with the following moiety:

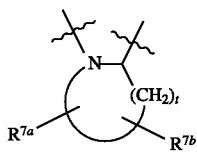

These reactions may be employed in a linear sequence to provide the compounds of the invention or they may be used to synthesize fragments which are subsequently joined by the reactions described in Reaction Schemes A–E.

The intermediates whose synthesis are illustrated in Reaction Schemes A and C can be reductively alkylated with a variety of aldehydes, such as I, as shown in Reaction Scheme F. The aldehydes can be prepared by standard procedures, such as that described by O. P. Goel, U. Krolls, M. Stier and S. Kesten in *Organic Syntheses*, 1988, 67, 69–75, from the appropriate amino acid (Reaction Scheme F). The reductive alkylation can be accomplished at pH 5–7 with a variety of reducing agents, such as sodium triacetoxyborohydride or sodium cyanoborohydride in a solvent such as dichloroethane, methanol or dimethylformamide. The product II can be deprotected to give the final compounds III with trifluoroacetic acid in methylene chloride. The final product III is isolated in the salt form, for example, as a trifluoroacetate, hydrochloride or acetate salt, among others. The product diamine III can further be selectively protected to obtain IV, which can subsequently be reductively alkylated with a second aldehyde to obtain V. Removal of the protecting group, and conversion to cyclized products such as the dihydroimidazole VII can be accomplished by literature procedures.

Alternatively, the protected dipeptidyl analog intermediate can be reductively alkylated with other aldehydes such as 1-trityl-4-carboxaldehyde or 1-trityl-4-imidazolylacetaldehyde, to give products such as VIII (Reaction Scheme G). The trityl protecting group can be removed from VIII to give IX, or alternatively, VIII can first be treated with an alkyl halide then subsequently deprotected to give the alkylated imidazole X. Alternatively, the dipeptidyl analog intermediate can be acylated or sulfonylated by standard techniques.

The imidazole acetic acid XI can be converted to the acetate XIII by standard procedures, and XIII can be first reacted with an alkyl halide, then treated with refluxing methanol to provide the regiospecifically alkylated imidazole acetic acid ester XIV. Hydrolysis and reaction with the protected dipeptidyl analog intermediate in the presence of condensing reagents such as 1-(3-dimethylaminopropyl)-3-ethylcarbodiimide (EDC) leads to acylated products such as XV.

If the protected dipeptidyl analog intermediate is reductively alkylated with an aldehyde which also has a protected hydroxyl group, such as XVI in Reaction Scheme I, the protecting groups can be subsequently removed to unmask the hydroxyl group (Reaction Schemes I, J). The alcohol can be oxidized under standard conditions to e.g. an aldehyde, which can then be reacted with a variety of organometallic reagents such as Grignard reagents, to obtain secondary alcohols such as XX. In addition, the fully deprotected amino alcohol XXI can be reductively alkylated (under conditions described previously) with a variety of aldehydes to obtain secondary amines, such as XXII (Reaction Scheme K), or tertiary amines.

The Boc protected amino alcohol XVIII can also be utilized to synthesize 2-aziridinylmethylpiperazines such as XXIII (Reaction Scheme L). Treating XVIII with 1,1'-sulfonyldiimidazole and sodium hydride in a solvent such as dimethylformamide led to the formation of aziridine XXIII. The aziridine reacted in the presence of a nucleophile, such as a thiol, in the presence of base to yield the ring-opened product XXIV.

In addition, the protected dipeptidyl analog intermediate can be reacted with aldehydes derived from amino acids such as O-alkylated tyrosines, according to standard procedures, to obtain compounds such as XXX, as shown in Reaction Scheme M. When R' is an aryl group, XXX can first be hydrogenated to unmask the phenol, and the amine group deprotected with acid to produce XXXI. Alternatively, the amine protecting group in XXX can be removed, and O-alkylated phenolic amines such as XXXII produced.

Similar procedures as are illustrated in Reaction Schemes F–M may be employed using other peptidyl analog intermediates such as those whose synthesis is illustrated in Reaction Schemes B–E.

Reaction Schemes N–R illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.
REACTION SCHEME F
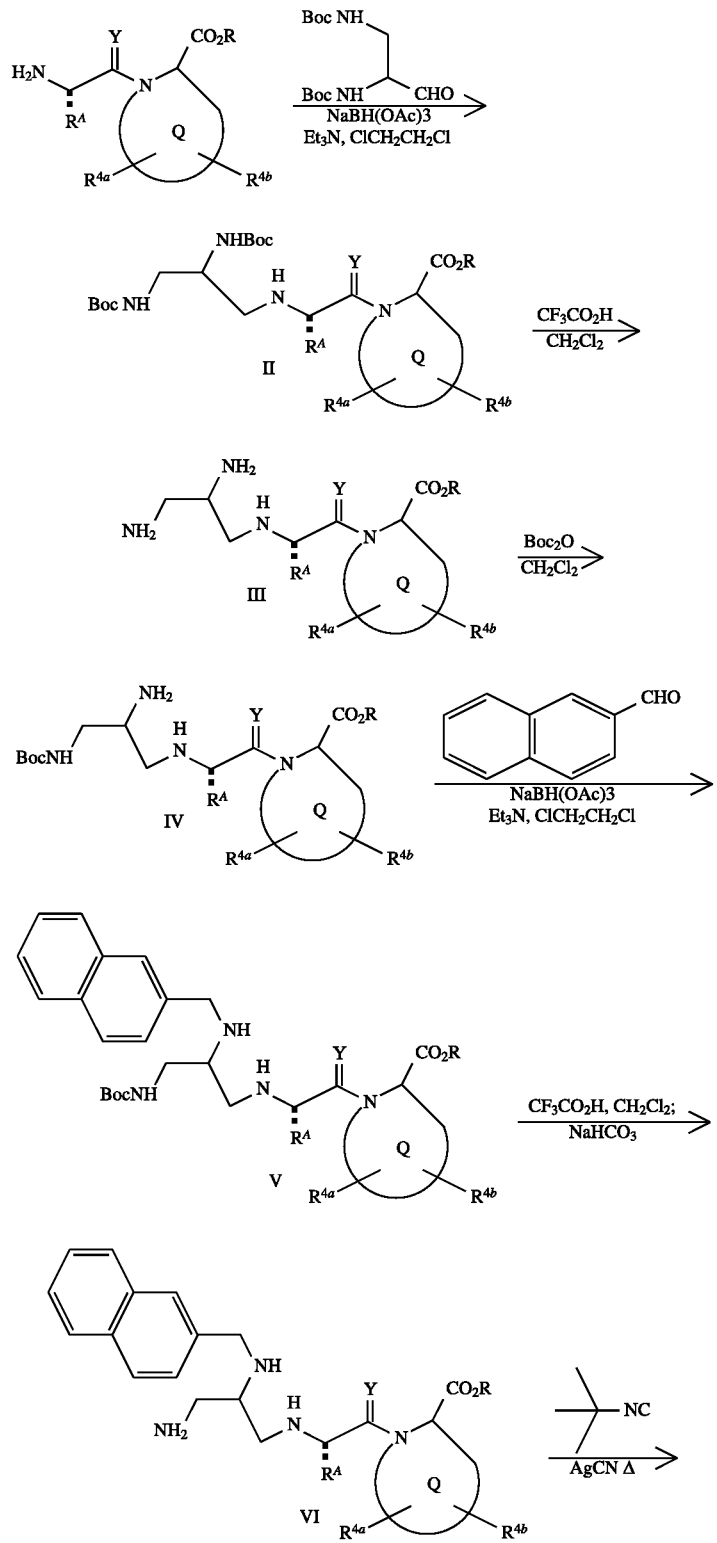

-continued
REACTION SCHEME F
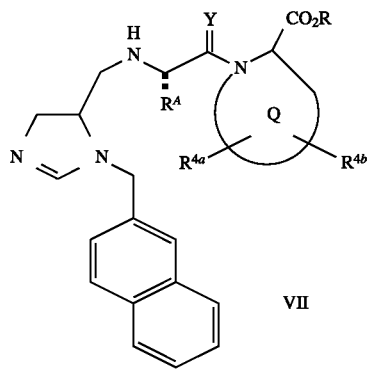
VII
REACTION SCHEME G
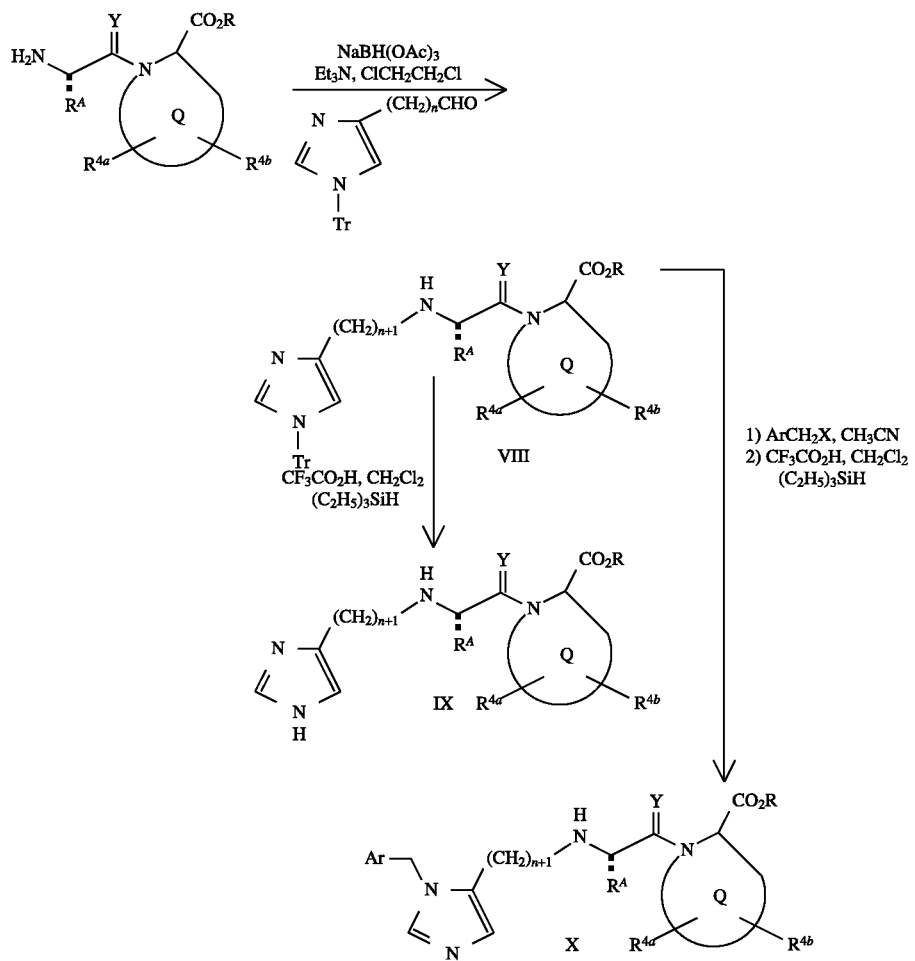

REACTION SCHEME H
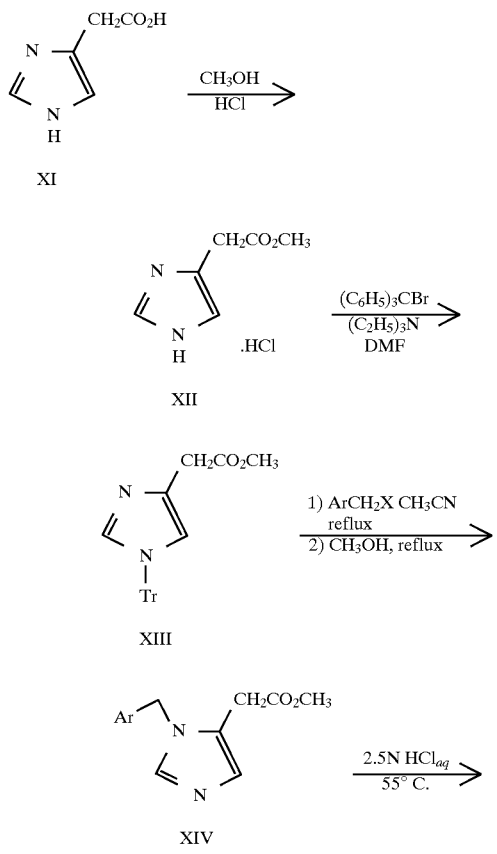
REACTION SCHEME I
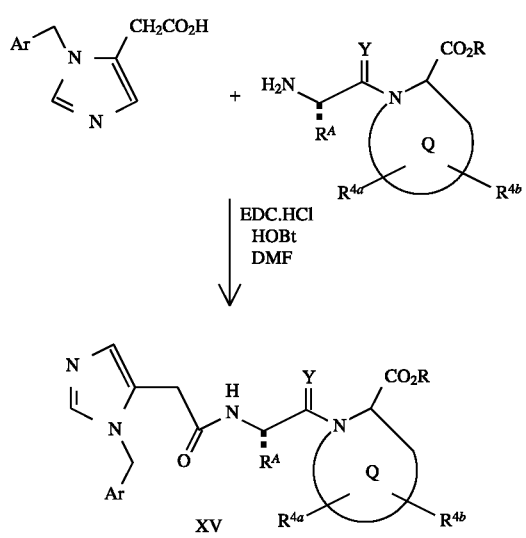
REACTION SCHEME J
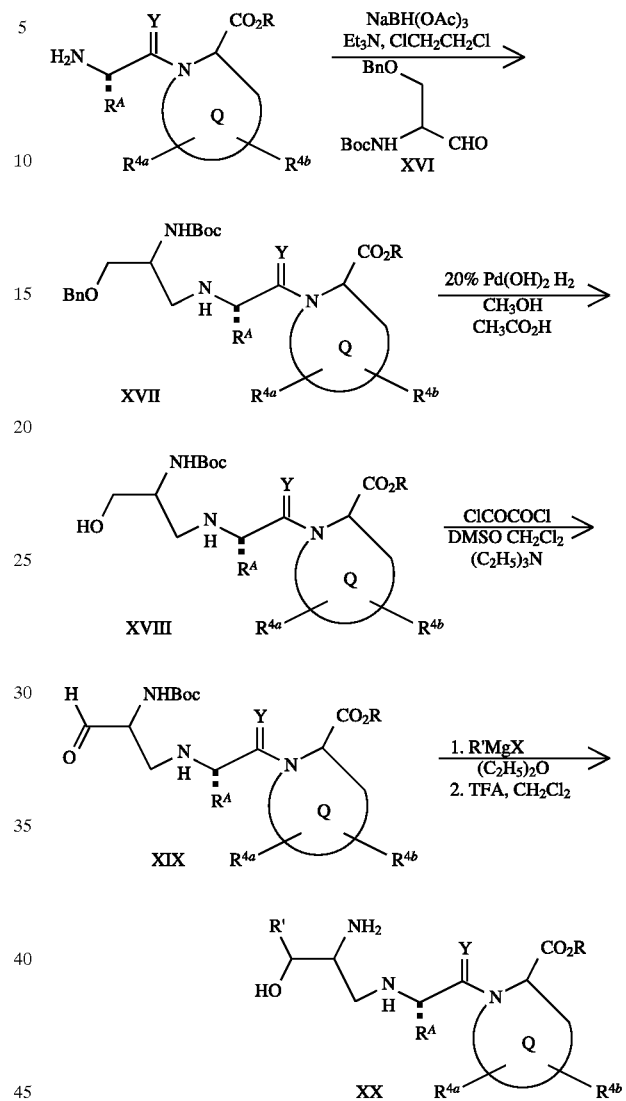
REACTION SCHEME K
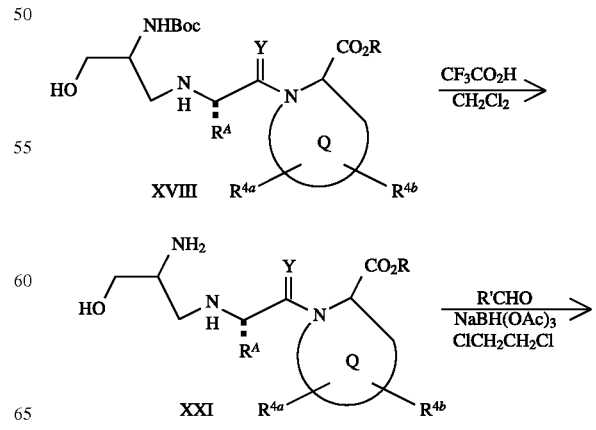

REACTION SCHEME K
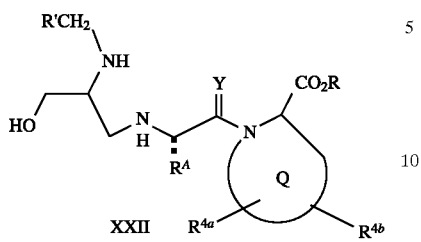
REACTION SCHEME L
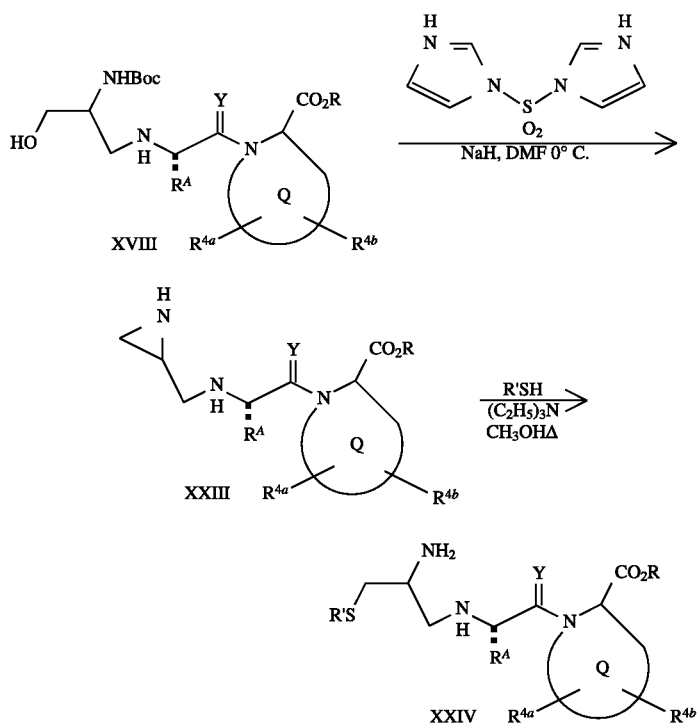
REACTION SCHEME M
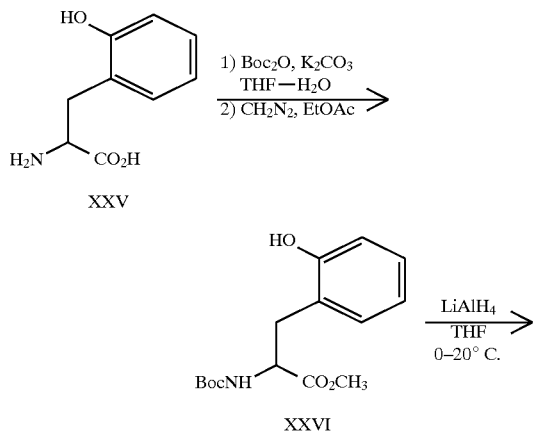

31
-continued
REACTION SCHEME M
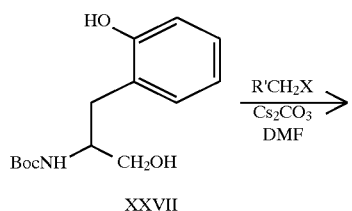
XXVII
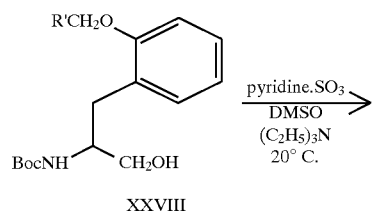
XXVIII
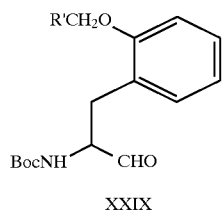
XXIX
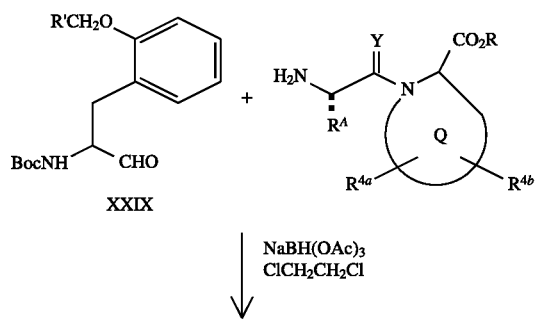
NaBH(OAc)$_3$
ClCH$_2$CH$_2$Cl
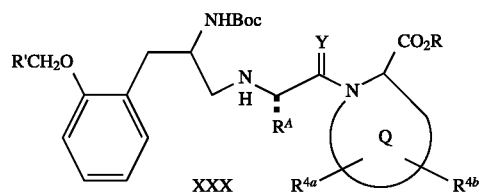
XXX
1) 20% Pd(OH)$_2$
   CH$_3$OH, CH$_3$CO$_2$H
2) HCl, EtOAc
HCl, EtOAc
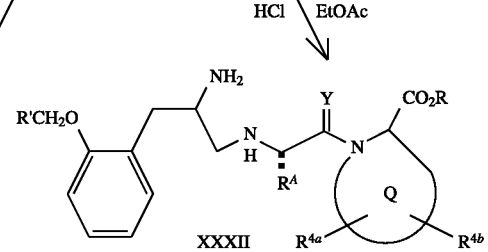
XXXII -continued
REACTION SCHEME M
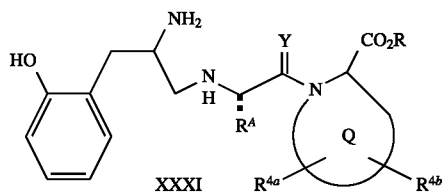
REACTION SCHEME N
REACTION SCHEME P
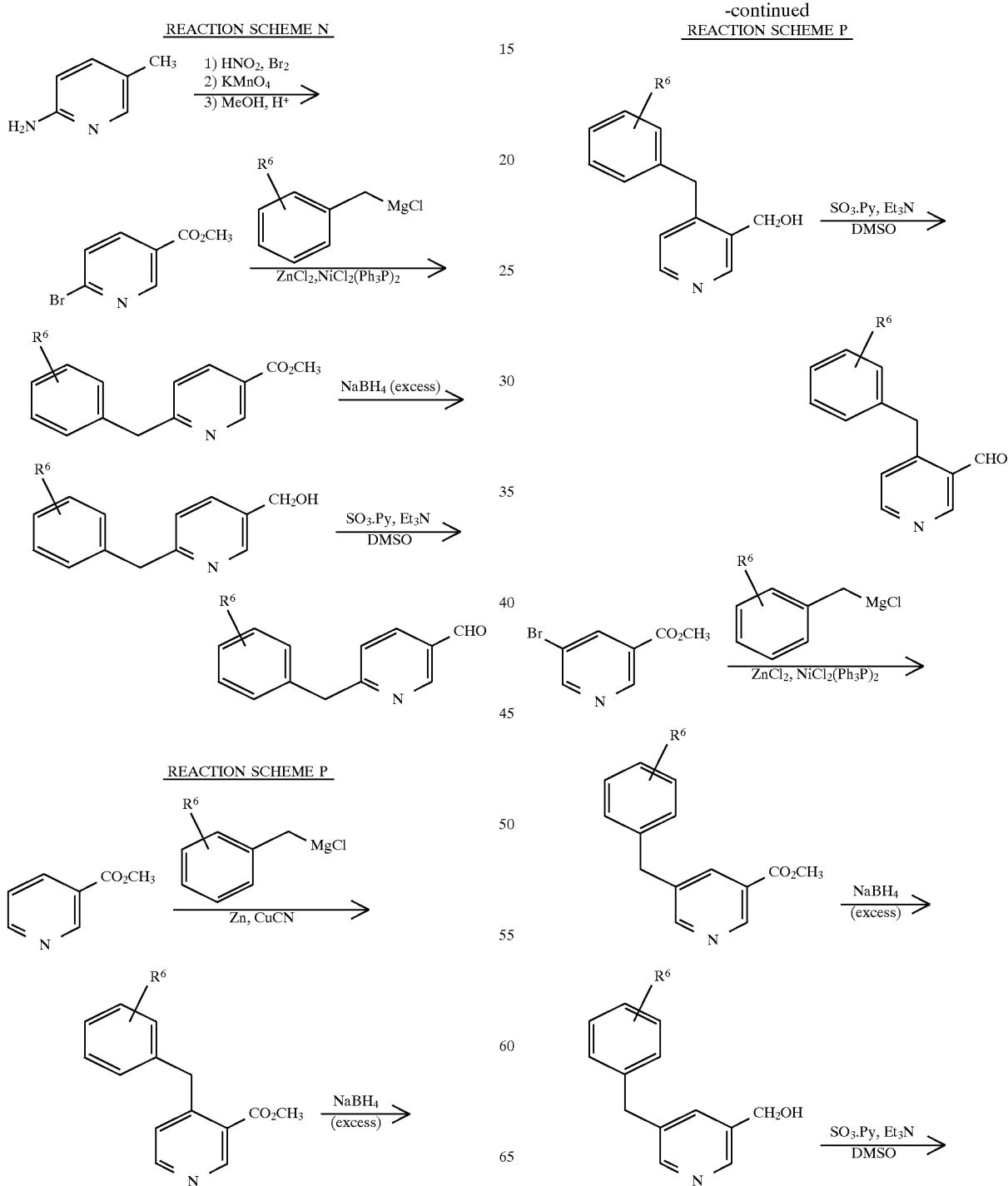

-continued
REACTION SCHEME P
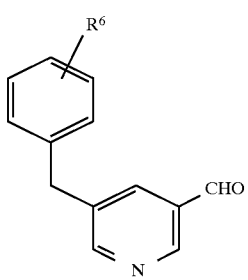
REACTION SCHEME O
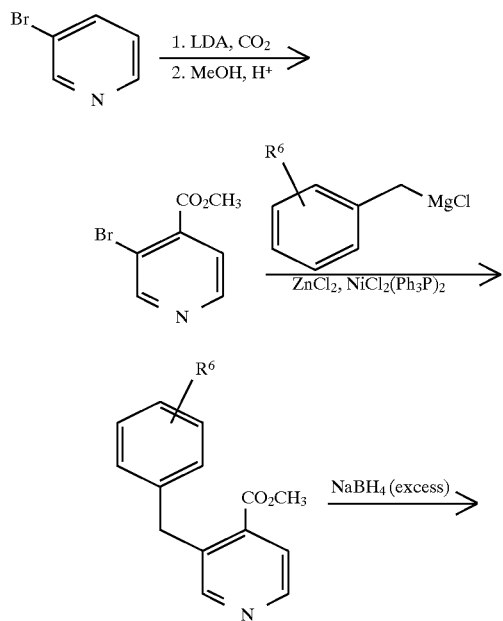
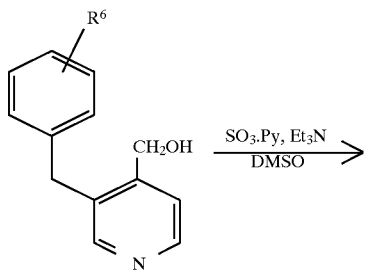
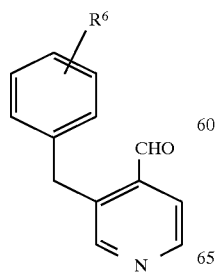
REACTION SCHEME R
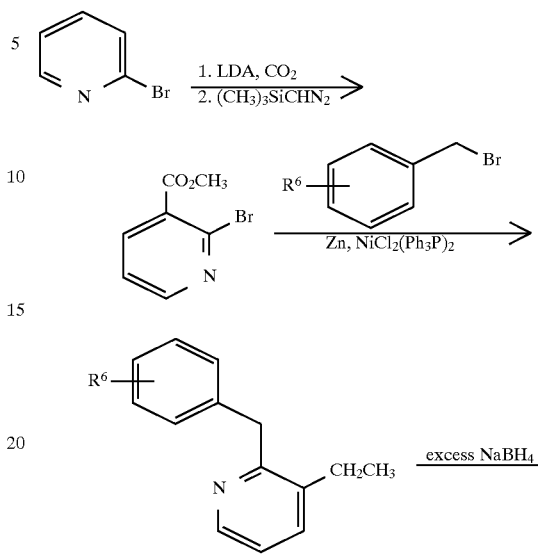
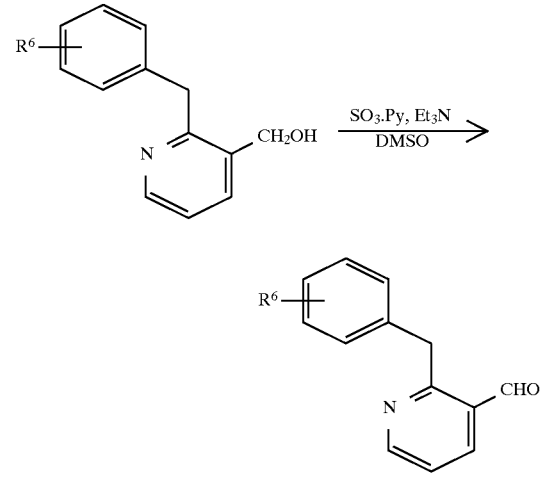
REACTION SCHEME S
Reaction S. Alkylation of an amide
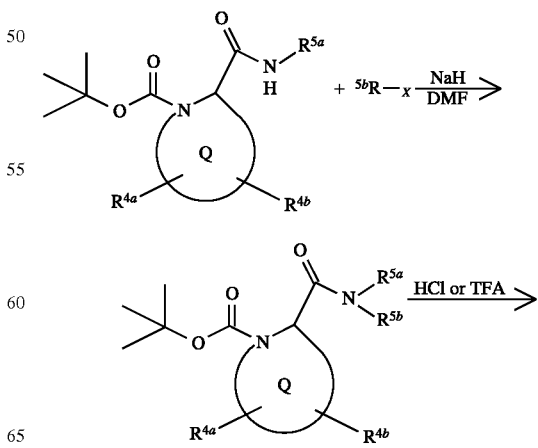

-continued
REACTION SCHEME S

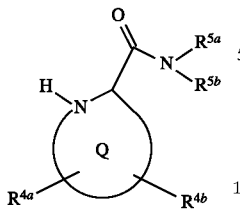

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras formation (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

The standard workup referred to in the examples refers to solvent extraction and washing the organic solution with 10% citric acid, 10% sodium bicarbonate and brine as appropriate. Solutions were dried over sodium sulfate and evaporated in vacuo on a rotary evaporator.

EXAMPLE 1

Preparation of N-[1-(3-[1H-Imidazol-4-yl] propionyl)-pyrrolidin-2(S)-ylmethyl]-3(S)-ethyl-proline-N-methyl-N-(3-chlorophenylmethyl) amide Step A: Diethyl 1-acetyl-5-hydroxy-3-ethylpyrrolidine-2,2-dicarboxylate Sodium (4.02 g, 0.175 mol) was dissolved in a stirred solution of diethyl acetamidomalonate (235.4 g, 1.19 mol) in abs EtOH (1.4 L) at ambient temperature under argon. The reaction mixture was cooled to 0° C., and trans-2-pentenal (100 g, 1.08 mol) was added dropwise maintaining the reaction temperature at <5° C. After the addition, the reaction was allowed to warm to room temperature, stirred for 4 h, then quenched with acetic acid (28 mL). The solution was concentrated in vacuo, and the residue dissolved in EtOAc (1.5 L), washed with 10% NaHCO$_3$ solution (2×300 mL), brine, and dried (MgSO$_4$). The solution was filtered and concentrated to 700 mL, then heated to reflux and treated with hexane (1 L). On cooling, the title compound precipitated and was collected, mp 106°–109° C. $^1$H NMR (CD$_3$OD) δ 5.65 (d, 1H, J=5 Hz), 4.1–4.25 (m, 4H), 2.7–2.8 (m, 1H), 2.21 (s, 3H), 2.10 (dd, 1H, J=6, 13, Hz),1.86–1.97 (m, 2H), 1.27 (t, 3H, J=7 Hz), 1.23 (t, 3H, J=7 Hz), 1.1–1.25 (m, 1H), 0.97 (t, 3H, J=7 Hz).

Step B: Diethyl 1-acetyl-3-ethylpyrrolidine-2,2-dicarboxylate

To a solution of diethyl 1-acetyl-5-hydroxy-3-ethyl-pyrrolidine-2,2-dicarboxylate (287 g, 0.95 mol) and triethylsilane (228 mL, 1.43 mol) in CH$_2$Cl$_2$ (3 L) under argon was added trifluoroacetic acid (735 mL, 9.53 mol) dropwise with stirring while maintaining the internal temperature at 25° C. by means of an ice bath. After stirring for 3 h at 23° C., the solution was concentrated in vacuo, the residue diluted with CH$_2$Cl$_2$ (1.5 L), then treated with H$_2$O (1 L) and solid Na$_2$CO$_3$ with vigorous stirring until the solution was basic. The organic layer was separated, dried (Na$_2$SO$_4$), filtered, then concentrated to give the title compound as a yellow oil which was used without further purification.

Step C: 3-Ethylproline hydrochloride (Cis:Trans Mixture)

Diethyl 1-Acetyl-3-ethylpyrrolidine-2,2-dicarboxylate (373 g, 0.95 mol) was suspended in 6N HCl (2 L) and HOAc (500 mL) and heated at reflux for 20 h. The reaction mixture was cooled, washed with EtOAc (1L), then concentrated in vacuo to give an oil which crystallized upon trituration with ether to give the title compound. $^1$H NMR (D$_2$O) δ 4.23 (d, 1H, J=8 Hz), 3.84 (d, 1H, J=8 Hz), 3.15–3.4 (m, 4H), 2.33–2.44 (m, 1H), 2.19–2.4 (m, 1H), 2.02–2.15 (m, 2H), 1.53–1.72 (m, 3H), 1.23–1.43 (m, 2H), 1.0–1.15 (m, 1H), 0.75–0.83 (m, 6H).

Step D: N-[(tert-Butyloxy)carbonyl]-cis:trans-3-ethylproline methyl ester

3-Ethylproline hydrochloride (Cis:Trans Mixture) (20 g, 0.11 mol) was dissolved in CH$_3$OH (200 mL), and the solution was saturated with HCl gas, then stirred at 23° C. for 24 h. Argon was bubbled through the solution to remove excess HCl. The solution was treated with NaHCO$_3$ (>84 g) to a pH of 8, then di-tert-butyl dicarbonate (25.1 g, 0.115 mol) dissolved in CH$_3$OH (20 mL) was added slowly. After stirring for 18 h at 23° C., the mixture was filtered, the filtrate concentrated, and the residue triturated with EtOAc, filtered again, and concentrated to give the title compound as an oil.

Step E: N-[(tert-Butyloxy)carbonyl]-trans-3-ethylproline and N-[(tert-Butyloxy)carbonyl]-cis-3-ethylproline methyl ester N-[(tert-Butyloxy)carbonyl]-cis,tranis-3-ethylproline methyl ester (29.1 g, 0.113 mol) was dissolved in CH$_3$OH (114 mL) with cooling to 0° C., then treated with 1N NaOH (114 mL). After stirring for 20 h at 23° C., the solution was concentrated to remove the CH$_3$OH and then extracted with EtOAc (3×). The organic layers were combined, dried (MgSO$_4$), filtered, and concentrated to give 12.8 g of N-[(tert-Butyloxy)carbonyl]-cis-3-ethylproline methyl ester as an oil. The aqueous layer was acidified with solid citric acid and extracted with EtOAc (2×), the organic layers combined, dried (MgSO$_4$), filtered, and concentrated to give N-[(tert-Butyloxy)carbonyl]-trans-3-ethylproline as an oil. $^1$H NMR (CD$_3$OD) δ 3.86 and 3.78 (2 d, 1H, J=6 Hz), 3.33–3.58 (m, 2H), 2.01–2.22 (m, 2H), 1.5–1.74 (m, 2H), 1.33–1.5 (m, 1H), 1.45 and 1.42 (2 s, 9H), 0.98 (t, 3H, J=8 Hz).

Step F: 3(S)-Ethyl-2(S)-proline hydrochloride

N-[(tert-Butyloxy)carbonyl]-trans-3-ethylproline (15.5 g, 0.064 mol), S-α-methylbenzylamine (9.03 mL, 0.070 mol), HOBT (10.73 g, 0.70 mol), and N-methylmorpholine (8 mL, 0.076 mol) were dissolved in CH$_2$Cl$_2$ (150 mL) with stirring in an ice-H$_2$O bath, treated with EDC (13.4 g, 0.070 mol) stirred at 23° C. for 48 h. The reaction mixture was partitioned between EtOAc and 10% citric acid solution, the organic layer washed with saturated NaHCO$_3$ solution, brine and dried (MgSO$_4$), filtered, and concentrated to give an oil. This oil was dissolved in a minimum amount of ether (10 mL) to crystallize the desired S,S,S diastereomer (4.2 g), mp 118°–121° C. A solution of this product in 8N HCl (87 mL) and glacial acetic acid (22 mL) was heated at reflux overnight. The solution was concentrated on a rotary evaporator, and the residue taken up in H$_2$O and extracted with ether. The aqueous layer was concentrated to dryness to give a 1:1 mixture of 3(S)-ethyl-2(S)-proline hydrochloride and α-methylbenzylamine.

3(S)-Ethyl-2(S)-proline containing α-methylbenzylamine (2.0 g, 0.0128 mol) was dissolved in dioxane (10 mL) and H$_2$O (10 mL) with stirring and cooling to 0° C. N,N-diisopropylethylamine (2.2 mL, 0.0128 mol) and di-tert-butyl-dicarbonate (2.79 g, 0.0128 mol) were added and stirring was continued at 23° C. for 48 h. The reaction mixture was partitioned between EtOAc (60 mL) and H$_2$O (30 mL), the organic layer washed with 0.5N NaOH (2×40 mL), the aqueous layers combined and washed with EtOAc (30 mL) and this layer back-extracted with 0.5N NaOH (30 mL). The aqueous layers were combined and carefully acidified at 0° C. with 1N HCl to pH 3. This mixture was extracted with EtOAc (3×40 mL), the organics combined, dried (MgSO$_4$), filtered and concentrated to give N-[(tert-Butyloxy)carbonyl-3(S)-ethyl-2(S)-proline as a colorless oil. N-[(tert-Butyloxy)carbonyl-3(S)-ethyl-2(S)-proline was dissolved in EtOAc (50 mL) and the solution was saturated with HCl gas with cooling in an ice-H$_2$O bath. The solution was stoppered and stirred at 0° C. for 3 hr. Argon was bubbled through the solution to remove excess HCl, and the solution was concentrated to dryness to give 3(S)-ethyl-2(S)-proline hydrochloride.

Step G: N-[(t-Butyloxycarbonyl)-pyrrolidin-2(S)-ylmethyl]-3(S)-ethyl-proline

3(S)-Ethyl-2(S)-proline hydrochloride (from Example 1, Step F) (2.33 g, 0.013 mol) was dissolved in CH$_3$OH (20 mL), treated with 3A molecular sieves (2 g) and KOAc (1.27 g, 0.013 mol) to adjust the pH of the reaction mixture to 4.5–5, then N-[(tert-Butyloxy) carbonyl-prolinal (Pettit et al., J. Org. Chem. (1994) 59, [21] 6287–95) (3.36 g, 0.017 mol) was added, and the mixture was stirred for 16 hours at room temperature. The reaction mixture was filtered, quenched with aqueous saturated NaHCO$_3$ (5 mL) and concentrated to dryness. The residue was extracted with CHCl$_3$. The extract was dried (MgSO$_4$), filtered, and concentrated to give the title compound and inorganic salts.

Step H: N-[(t-Butyloxycarbonyl)-pyrrolidin-2(S)-ylmethyl]-3(S)-ethyl-proline-N-(3-chlorophenylmethyl) amide N-[(t-Butyloxycarbonyl)-pyrrolidin-2(S)-ylmethyl]-3(S)-ethyl-proline (0.50 g, 1.53 mmol), EDC (0.293 g, 1.53 mmol), HOBT (0.243 g, 1.53 mmol) and 3-chlorobenzylamine(0.187 mL, 1.53 mmol) were dissolved in DMF (5 mL), the pH adjusted to 7 with N-methylmorpholine (0.51 mL, 4.6 mmol), and the reaction mixture stirred for 18 hours at ambient temperature. After removing the solvent in vacuo the residue was partitioned between EtOAc and 5% aqueous NaHCO$_3$. The organic layer was washed with brine, dried (MgSO$_4$), filtered, and concentrated to give the title compound after chromatography (SiO$_2$, EtOAc:hexane, 2:3).

Step I: N-[(t-Butyloxycarbonyl)-pyrrolidin-2(S)-ylmethyl]-3(S)-ethyl-proline-N-methyl-N-(3-chlorophenylmethyl) amide N-[(t-Butyloxycarbonyl)-pyrrolidin-2(S)-ylmethyl]-3(S)-ethyl-proline-N-(3-chlorophenylmethyl) amide (0.175 g, 0.39 mmol) was dissolved in dry DMF (4 mL) with stirring at 0° C. under Ar, treated with NaH (60% dispersion in mineral oil, 0.023 g, 0.58 mmol), and after 15 minutes treated with iodomethane (0.029 mL, 0.47 mmol). The reaction mixture was stirred at 25° C. for 2 h, then evaporated to dryness and partitioned between EtOAc and aqueous saturated NaHCO$_3$ solution. The organic layer was separated, washed with brine, dried (MgSO$_4$), filtered, and concentrated to dryness to give the title compound.

Step J: (Pyrrolidin-2(S)-ylmethyl)-3(S)-ethyl-proline-N-methyl-N-(3-chlorophenylmethyl) amide N-[(t-Butyloxycarbonyl)-pyrrolidin-2(S)-ylmethyl]-3(S)-ethyl-proline-N-methyl-N-(3-chlorophenylmethyl) amide (0.150 g, 0.32 mmol) was dissolved in EtOAc (15 mL), cooled to −20° C. and saturated with HCl gas. The solution was stirred at 0° C. for 1 h, then at 25° C. for 1 hour, then concentrated to dryness to give pyrrolidin-2(S)-ylmethyl]-3(S)-ethyl-proline-N-methyl-N-(3-chlorophenylmethyl) amide which was used without further purification.

Step K: N-[1-(3-[1H-Imidazol-4-yl]propionyl)-pyrrolidin-2(S)-ylmethyl]-3(S)-ethyl-proline-N-(3-chlorophenylmethyl) amide (Pyrrolidin-2(S)-ylmethyl)-3(S)-ethyl-proline-N-methyl-N-(3-chlorophenylmethyl) amide (0.070 g, 0.162 mmol), 1 H-imidazol-4-yl]propionic acid hydrochloride (0.057 g, 0.324 mmol), EDC (0.062 g, 0.324 mmol), HOBT (0.050 g, 0.324 mmol), and N-methylmorpholine (0.288 mL, 1.30 mmol) were dissolved in DMF (5 mL) at 25° C. and stirred for 72 h. The reaction mixture was partitioned between EtOAc and 5% Na$_2$CO$_3$ solution, the organic layer separated, washed with brine, dried (MgSO$_4$), filtered, and concentrated to dryness to give the title compound after preparative RP HPLC (Vydac column, 0.1% TFA/CH$_3$CN:0.1% TFA/H$_2$O, 95:5 to 5:95 gradient) and lyophilization. to give the title compound as the TFA salt.

Anal. calcd for $C_{26}H_{36}N_5O_2Cl \cdot 1.9\ CF_3CO_2H \cdot 2.0\ H_2O$: C, 48.45; H, 5.72; N, 9.48; found: C, 48.53; H, 5.76; N, 9.08. FAB MS 486 (M+1)

EXAMPLE 2

Preparation of N-[1-(3[1H-Imidazol-4-yl]propionyl)-3(S)-ethylpyrrolidin-2(S)-ylmethyl]-3(S)-ethyl-proline-N-methyl-N-(3-chlorophenylmethyl) amide Step A: N-[(tert-Butyloxy)carbonyl]-3(S)-ethyl-2(S)-prolinol 3(S)-Ethyl-2(S)-proline hydrochloride (Example 1, Step G) containing α-methylbenzylamine (2.0 g, 0.0128 mol) was dissolved in dioxane (10 mL) and H$_2$O (10 mL) with stirring and cooling to 0° C. N,N-diisopropylethylamine (2.2 mL, 0.0128 mol) and di-tert-butyl-dicarbonate (2.79 g, 0.0128 mol) were added and stirring was continued at 23° C. for 48 h. The reaction mixture was partitioned between EtOAc (60 mL) and H$_2$O (30 mL), the organic layer washed with 0.5N NaOH (2×40 mL), the aqueous layers combined and washed with EtOAc (30 mL) and this layer back-extracted with 0.5N NaOH (30 mL). The aqueous layers were combined and carefully acidified at 0° C. with 1N HCl to pH 2. This mixture was extracted with EtOAc (3×40 mL), the organics combined, dried (MgSO$_4$), filtered and concentrated to give N-[(tert-Butyloxy)carbonyl-3(S)-ethyl-2(S)-proline as a colorless oil which was used without purification.

N-[(tert-Butyloxy)carbonyl]-3(S)-ethyl-2(S)-proline (1.6 g, 6.58 mmol) was dissolved in dry THF (10 mL) and treated with borane (1M in THF, 12.5 mL, 12.5 mmol) with stirring at 0° C. for 2 h, then 23° C. for 1 h. The solution was cooled to 0° C., treated with H$_2$O (20 mL), and extracted with EtOAc (2×30 mL). The organics were washed with brine, saturated NaHCO$_3$, H$_2$O, dried (MgSO$_4$), filtered and concentrated to give a viscous oil. The oil was dissolved in CH$_2$Cl$_2$, filtered through dry SiO$_2$, and the filtrate concentrated to give the title compound as an oil. $^1$H NMR (CDCl$_3$) δ 4.97 (d, 1H, J=7 Hz), 3.71 (t, 1H, J=8 Hz), 3.51–3.62 (m, 3H), 3.18–3.26 (m, 1H), 1.9–2.0 (m, 1H), 1.53–1.7 (m, 2H), 1.47 (s, 9H), 1.26–1.43 (m, 2H), 0.95 (t, 3H, J=7 Hz).

Step B: N-[(tert-Butyloxy)carbonyl]-3(S)-ethyl-2(S)-prolinal

N-[(tert-Butyloxy)carbonyl-3(S)-ethyl-2(S)-prolinol (0.638 g, 2.78 mmol) and Et$_3$N (1.4 mL, 9.74 mmol) were dissolved in dry CH$_2$Cl$_2$ (10 mL) with stirring and cooling to −10° C. and treated dropwise with a solution of SO$_3$·pyr (1.33 g, 8.35 mmol) in dry DMSO (5 mL) keeping the reaction mixture temperature at <0° C. The mixture was stirred at 0° C. for 20 minutes then at 5° C. for 20 minutes, and at 15° C. for 1 hour, then poured into ice-cold 0.5N HCl and the layers separated. The aqueous layer was extracted with CH$_2$Cl$_2$ (3–20 mL), organics combined, washed with H$_2$O, aqueous saturated NaHCO$_3$ solution, brine, and dried (Na$_2$SO$_4$). Filtration and concentration to dryness gave the title compound which was used without purification.

Step C: N-[(t-Butyloxycarbonyl)-3(S)-ethylpyrrolidin-2(S)-ylmethyl]-3 (S)-ethyl-proline Following the procedure outlined in Example 1, Step G, but substituting N-[(tert-butyloxy)carbonyl]-3(S)-ethyl-2(S)-prolinal for N-[(tert-Butyloxy)carbonyl]-2(S)-prolinal the title compound was prepared.

Step D: N-[1-(3-[1H-Imidazol-4-yl]propionyl)-3(S)-ethylpyrrolidin-2(S)-ylmethyl]-3(S)-ethyl-proline-N-methyl-N-(3-chlorophenylmethyl) amide Using the procedures described in Example 1, the title compound is prepared.

EXAMPLE 3

Preparation of 1-[1-(4-Cyanobenzyl)-1H-imidazol-5-ylacetyl]pyrrolidin-2(S)-ylmethyl]-3(S)-ethyl-proline-N-methyl-N-(3-chlorophenylmethyl) amide Step A: 1H-Imidazole-4-acetic acid methyl ester hydrochloride A solution of 1H-imidazole-4-acetic acid hydrochloride (4.00 g, 24.6 mmol) in methanol (100 ml) was saturated with gaseous hydrogen chloride. The resulting solution was allowed to stand at room temperature (RT) for 18 hours. The solvent was evaporated in vacuo to afford the title compound as a white solid.

$^1$H NMR(CDCl$_3$, 400 MHz) δ 8.85(1H, s), 7.45(1H, s), 3.89(2H, s) and 3.75(3H, s) ppm.

Step B: 1-(Tribenzyl)-1H-imidazol-4-ylacetic acid methyl ester

To a solution of 1H-Imidazole-4-acetic acid methyl ester hydrochloride (24.85 g, 0.141mol) in dimethyl formamide (DMF) (11 ml) was added triethylamine (57.2 ml, 0.412 mol) and tribenzyl bromide(55.3 g, 0.171 mol) and the suspension was stirred for 24 hours. After this time, the reaction mixture was diluted with ethyl acetate (EtOAc) (11) and water (350 ml). The organic phase was washed with saturated. aqueous. NaHCO$_3$ (350 ml), dried (Na$_2$SO$_4$) and evaporated in vacuo. The residue was purified by flash chromatography (SiO$_2$, $_{0-100}$% ethyl acetate in hexanes; gradient elution) to provide the title compound as a white solid.

$^1$H NMR (CDCl$_3$, 400 MHz) δ 7.35(1H, s), 7.31(9H, m), 7.22(6H, m), 6.76(1H, s), 3.68(3H, s) and 3.60(2H, s) ppm.

Step C: [1-(4-Cyanobenzyl)-1H-imidazol-5-yl]acetic acid methyl ester

To a solution of 1-(Tribenzyl)-1H-imidazol-4-ylacetic acid methyl ester (8.00 g, 20.9 mmol) in acetonitrile (70 ml) was added bromo-p-toluonitrile (4.10 g, 20.92 mmol) and heated at 55° C. for 3 hr. After this time, the reaction was cooled to room temperature and the resulting imidazolium salt (white precipitate) was collected by filtration. The filtrate was heated at 55° C. for 18 hours. The reaction mixture was cooled to room temperature and evaporated in vacuo. To the residue was added EtOAc (70 ml) and the resulting white precipitate collected by filtration. The precipitated imidazolium salts were combined, suspended in methanol (100 ml) and heated to reflux for 30 minutes. After this time, the solvent was removed in vacuo, the resulting residue was suspended in EtOAc (75 ml) and the solid isolated by filtration and washed (EtOAc). The solid was treated with saturated aqueous NaHCO$_3$ (300 ml) and CH$_2$Cl$_2$ (300 ml) and stirred at room temperature for 2 hr. The organic layer was separated, dried (MgSO$_4$) and evaporated in vacuo to afford the title compound as a white solid:

$^1$H NMR(CDCl$_3$, 400 MHz) δ 7.65(1H, d, J=8 Hz), 7.53(1H, s), 7.15(1H, d, J=8 Hz), 7.04(1H, s), 5.24(2H, s), 3.62(3H, s) and 3.45(2H, s) ppm.

Step D: [1-(4-Cyanobenzyl)-1H-imidazol-5-yl]acetic acid

A solution of [1-(4-cyanobenzyl)-1H-imidazol-5-yl] acetic acid methyl ester (4.44 g, 17.4 mmol ) in THF (100 ml) and 1M lithium hydroxide (17.4 ml, 17.4 mmol) was stirred at RT for 18 hr. 1M HCl (17.4 ml) was added and the THF was removed by evaporation in vacuo. The aqueous solution was lyophilized to afford the title compound containing lithium chloride as a white solid.

$^1$H NMR(CD$_3$OD, 400 MHz) δ 8.22(1H, s), 7.74(1H, d, J=8.4 Hz), 7.36(1H, d, J=8.4 Hz), 7.15(1H, s), 5.43(2H, s) and 3.49(2H, s) ppm.

Step E: 1-[1-(4-Cyanobenzyl)-1H-imidazol-5-ylacetyl]pyrrolidin-2(S)-ylmethyl]-3(S)-ethyl-proline-N-methyl-N-(3-chlorophenylmethyl) amide Pyrrolidin-2(S)-ylmethyl]-3(S)-ethyl-proline-N-methyl-N-(3-chlorophenylmethyl) amide (0.070 g, 0.162 mmol) (Example 1, Step J), [1-(4-cyanobenzyl)-1H-imidazol-5-yl] acetic acid.LiCl (0.093 g, 0.324 mmol), EDC (0.062 g, 0.324 mmol), HOBT (0.050 g, 0.324 mmol), and N-methylmorpholine (0.288 mL, 1.30 mmol) were dissolved in DMF (5 mL) at 25° C. and stirred for 72 h. The reaction mixture was partitioned between EtOAc and 5% Na$_2$CO$_3$ solution, the organic layer separated, washed with brine, dried (MgSO$_4$), filtered, and concentrated to dryness to give the title compound after preparative RP HPLC (Vydac column, 0.1% TFA/CH$_3$CN: 0.1% TFA/H$_2$O, 95:5 to 5:95 gradient) and lyophilization. to give the title compound as the TFA salt. $^1$H NMR (CD$_3$OD, 400 MHz) δ 8.96 and 8.93 (1H, 2 s, 1:2 ratio), 7.78 –7.85 (2H, m), 7.5–7.62 (3H, m), 7.2–7.4 (4H, m), 5.60 and 5.67 (2H, 2 s, 1:2 ratio), 4.55–4.8 (2H, m), 4.09–4.2 (1H, m), 3.82–4.0 (3H, m), 3.5–3.65 (2H, m), 3.35–3.49 (2H, m), 3.18–3.3 (1H, m), 3.10 (3H, s), 2.1–2.4 (4H, m), 1.92–2.09 (3H, m), 1.71–1.92 (2H, m), 1.5–1.7 (1H, m), 0.96–1.08 (3H, m) ppm. FAB MS 587 (M+1)

EXAMPLE 4

Preparation of 1-[1-(4-Cyanobenzyl)-1H-imidazol-5-ylacetyl]pyrrolidin-2(S)-ylmethyl]-3(S)-ethyl-proline-N-(3-chlorophenylmethyl) amide Step A: (Pyrrolidin-2(S)-ylmethyl)-3(S)-ethyl-proline-N-(3-chlorophenylmethyl) amide N-[(t-Butyloxycarbonyl)-pyrrolidin-2(S)-ylmethyl]-3(S)-ethyl-proline-N-(3-chlorophenylmethyl) amide (Example 1, Step H) (0.175 g, 0.39 mmol) was dissolved in EtOAc (15 mL), cooled to −20° C. and saturated with HCl gas. The solution was stirred at 0° C. for 1 h, then at 25° C. for 1 h, then concentrated to dryness to give pyrrolidin-2(S)-ylmethyl]-3(S)-ethyl-proline-N-(3-chlorophenylmethyl) amide which was used without further purification.

Step B: 1-[1-(4-Cyanobenzyl)-1H-imidazol-5-ylacetyl] pyrrolidin-2(S)-ylmethyl]-3(S)-ethyl-proline-N-(3-chlorophenylmethyl) amide Using the procedures described in Example 3, but substituting pyrrolidin-2(S)-ylmethyl]-3(S)-ethyl-proline-N-(3-chlorophenylmethyl) amide for pyrrolidin-2(S)-ylmethyl]-3 (S)-ethyl-proline-N-methyl-N-(3-chlorophenylmethyl) amide in Step E, the title compound was prepared. $^1$H NMR (CD$_3$OD, 400 MHz) δ 8.94 (1H, s), 7.81 (2H, d, J=5 Hz), 7.5–7.6 (3H, m), 7.12–7.38 (4H, m), 5.55 (2H, s), 4.38–4.54 (2H, m), 4.02–4.18 (1H, m), 3.75–4.01 (4H, m), 3.42–3.65 (2H, m), 3.42–3.65 (2H, m), 3.1–3.27 (1H, m), 2.2–2.4 (2H, m), 1.6–2.2 (7H, m), 1.42–1.58 (1H, m), 1.22–1.35 (1H, m), 0.95–1.08 (3H, m) ppm. FAB MS 573 (M+1)

EXAMPLE 5

Preparation of 1-(1-(4-Nitrobenzyl)-1H-imidazol-4-ylacetyl]pyrrolidin-2(S)-ylmethyl]-3(S)-ethyl-proline-N-methyl-N-(3-chlorophenylmethyl) amide and 1-[1-(4-Nitrobenzyl)-1H-imidazol-5-ylacetyl] pyrrolidin-2(S)-ylmethyl]-3(S)-ethyl-proline-N-methyl-N-(3-chlorophenylmethyl) amide Step A: 1-(4-Nitrobenzyl)-1H-imidazol-4-ylacetic acid methyl ester and 1-(4-Nitrobenzyl)-1H-imidazol-5-ylacetic acid methyl ester (3:1 mixture)

To a solution of sodium hydride (60% in mineral oil, 99 mg, 2.5 mmol) in dimethylformamide (2 ml) cooled to 0° C. was added, via cannula, a solution of 1H-imidazole-4-acetic acid methyl ester hydrochloride (200 mg, 1.13 mmol) in dimethylformamide (3 ml). This suspension was allowed to stir at 0° C. for 15 min. To this suspension was added 4-nitrobenzyl bromide (244 mg, 1.13 mmol) and stirred at room temperature for 2 h. After this time, the mixture was quenched with saturated. aqueous. sodium bicarbonate (15 ml) and water (20 ml) and extracted with methylene chloride (2×50 ml). The combined organic extracts were washed with brine (20 ml), dried (MgSO$_4$), filtered and the solvent was evaporated in vacuo. The residue was purified by flash chromatography using acetonitrile as eluent to give the title compounds as a yellow oil.

$^1$H NMR (CDCl$_3$, 400 MHz) δ 8.20 (2H, d, J=8.5 Hz), 7.49 (1H, s), 7.27 (2H, d, J=8.5 Hz), 7.03 (0.25H, s), 6.87 (0.75H, s), 5.28 (0.5H, s), 5.18 (1.5H, s), 3.70 (2.25H, s), 3.65 (1.5H, s), 3.61 (0.75H, s) and 3.44 (0.5H, s) ppm.

Step B: 1-(4-Nitrobenzyl)-1H-imidazol-4-ylacetic acid hydrochloride and 1-(4-Nitrobenzyl)-1H-imidazol-5-ylacetic acid (3:1 mixture)

To a solution of a mixture of 1-(4-Nitrobenzyl)-1H-imidazol-4-ylacetic acid methyl ester and 1-(4-Nitrobenzyl)-1H-imidazol-5-ylacetic acid methyl ester (3:1 mixture, 216 mg, 0.785 mmol) in methanol (3 ml) and tetrahydrofuran (3 ml) under argon was added 1.0M sodium hydroxide (1.18 ml, 1.1 8 mmol) and stirred for 18 h. After this time, 1.0N hydrochloric acid (2.36 ml, 2.36 mmol) was added and the mixture evaporated in vacuo to give the title compounds.

$^1$H NMR (CDCl$_3$, 400 MHz) δ 9.04 (0.75H, s), 8.83 (0.25H, s), 8.28 (2H, d, J=8.8 Hz), 7.61 (2H, d, J=8.8 Hz), 7.54 (0.75H, s), 7.43 (0.25H, s), 5.61 (0.5H, s), 5.58 (1.5H, s), 3.84 (0.5H, s) and 3.82 (1.5H, s) ppm.

Step C: 1-(1-(4-Nitrobenzyl)-1H-imidazol-4-ylacetyl]pyrrolidin-2(S)-ylmethyl]-3(S)-ethyl-proline-N-methyl-N-(3-chlorophenylmethyl) amide and 1-[1-(4-Nitrobenzyl)-1H-imidazol-5-ylacetyl]pyrrolidin -2(S)-ylmethyl]-3(S)-ethyl-proline-N-(3-chlorophenylmethyl) amide Using the procedures outlined in Examples 3 and 4, the title compounds are prepared.

The following compounds are prepared in a similar manner:

1-(1-(4-Nitrobenzyl)-1H-imidazol-4-ylacetyl]pyrrolidin-2(S)-ylmethyl]-3(S)-ethyl-proline-N-(3-chlorophenylmethyl) amide 1-[1-(4-Nitrobenzyl)-1H-imidazol-5-ylacetyl]pyrrolidin-2(S)-ylmethyl]-3(S)-ethyl-proline-N-(3-chlorophenylmethyl) amide 1-(1-(4-Methoxybenzyl)-1H-imidazol-5-ylacetyl) pyrrolidin-2(S)-ylmethyl]3(S)-ethyl-proline-N-methyl-N-(3-chlorophenylmethyl) amide 1-(1-(4-Methoxybenzyl)-1H-imidazol-5-ylacetyl) pyrrolidin-2(S)-ylmethyl]-3(S)-ethyl-proline-N-(3-chlorophenylmethyl) amide 1-(1-(2-Naphthylmethyl)-1H-imidazol-5-ylacetyl] pyrrolidin-2(S)-ylmethyl]-3(S)-ethyl-proline-N-methyl-N-(3-chlorophenylmethyl) amide 1-(1-(2-Naphthylmethyl)-1H-imidazol-5-ylacetyl] pyrrolidin-2(S)-ylmethyl]-3(S)-ethyl-proline-N-(3-chlorophenylmethyl) amide

EXAMPLE 6

Preparation of 1-(1-(1-Farnesyl)-1H-imidazol-5-ylacetyl)-pyrrolidin-2(S)-ylmethyl]-3(S)-ethyl-proline-N-methyl-N-(3-chlorophenylmethyl) amide Step A: 1-(1-Farnesyl)-1H-imidazol-5-ylacetic acid methyl ester To a solution of 1-(tribenzyl)-1H-imidazol-4-ylacetic acid methyl ester (200 mg, 0.523 mmol) in acetonitrile (5 ml) was added trans, trans-farnesyl bromide (156 μl, 0.575 mmol) and heated at 55° C. for 16 h. After this time, the reaction was heated at 80° C. for 3 h and then the reaction mixture was evaporated in vacuo. The residue was dissolved in methanol (5 ml) and heated to reflux for 30 minutes and then evaporated in vacuo. The residue was purified by flash chromatography (2–4% methanol/methylene chloride gradient elution) to provide the title compound.

$^1$H NMR (CDCl$_3$, 400 MHz) δ 7.50 (1H, s), 6.92 (1H, s), 5.24 (1H, t, J=5.9 Hz), 5.09 (2H, m), 4.49 (2H, d, J=6.9 Hz), 3.69 (3H, s), 3.60 (2H, s), 1.91–2.15 (8H, m), 1.72 (3H, s), 1.65 (3H, s), 1.59 (3H, s) and 1.57 (3H, s) ppm.

Step B: 1-(1-(1-Farnesyl)-1H-imidazol-5-ylacetyl)-pyrrolidin-2(S)-ylmethyl]-3(S)-ethyl-proline-N-methyl-N-(3-chlorophenylmethyl) amide Following the procedure described in Example 5, but using 1-farnesyl-1H-imidazol-5-ylacetic acid methyl ester described in Step A in place of 1-(4-nitrobenzyl)-1H-imidazol-5-ylacetic acid methyl ester provides the title compound.

1-(1-(1-Geranyl)-1H-imidazol-5-ylacetyl)-pyrrolidin-2 (S)-ylmethyl]-3(S)-ethyl-proline-N-methyl-N-(3-chlorophenylmethyl) amide is prepared in a similar manner.

EXAMPLE 7

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μm ZnCl$_2$ and 100 nm Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention were tested for inhibitory activity against human FPTase by the assay described above and were found to have IC$_{50}$ of <10 μM.

EXAMPLE 8

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemeted with 10% regular DMEM, 2% fetal bovine serum and 400 mCi[$^{35}$S] methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and auto-radiographed. The intensities of the bands corresponding to farnesylated and nonfarnesylated ras proteins are compared to determine the percent inhibition of farnesyl transfer to protein.

EXAMPLE 9

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound illustrated by the formula

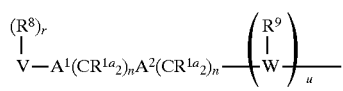

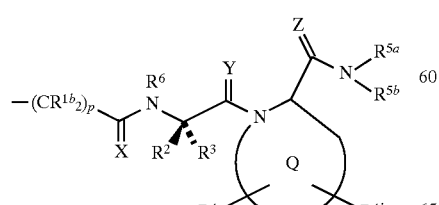

wherein:

$R^{1a}$ is independently selected from: hydrogen or $C_1$–$C_6$ alkyl;

$R^{1b}$ is independently selected from:
a) hydrogen,
b) aryl, heterocycle, cycloalkyl, $R^{10}O$—, —$N(R^{10})_2$ or alkenyl,
c) $C_1$–$C_6$ alkyl unsubstituted or substituted by aryl, heterocycle, cycloalkyl, alkenyl, $R^{10}O$—, or —$N(R^{10})_2$;

$R^2$ and $R^3$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{10}$ alkyl, $C_2$–$C_{10}$ alkenyl, $C_3$–$C_{10}$ cycloalkyl, aryl or heterocyclic group,
  wherein the substituent is selected from F, Cl, Br, NO$_2$, $R^{10}O$—, $R^{11}S(O)_m$—, $R^{10}C(O)NR^{10}$—, CN, $(R^{10})_2N$—$C(NR^{10})$—, $R^{10}C(O)$—, CON$(R^{10})_2$—, N$_3$, —$N(R^{10})_2$, $R^{11}OC(O)NR^{10}$— and $C_1$–$C_{20}$ alkyl, and
d) $C_1$–$C_6$ alkyl substituted with an unsubstituted or substituted group selected from aryl, heterocycle and $C_3$–$C_{10}$ cycloalkyl;

or $R^2$ or $R^3$ are combined with $R^6$ to form a ring such that

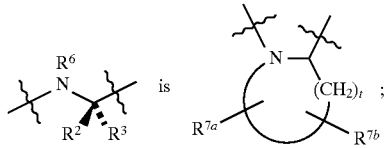

$R^{4a}$ sand $R^{7a}$ independently selected from:
a) hydrogen,
b) $C_1$–$C_6$ alkyl unsubstituted or substituted by alkenyl, $R^{10}O$—, $R^{11}S(O)_m$—, $R^{10}C(O)NR^{10}$—, CN, N$_3$, $(R^{10})_2N$—$C(NR^{10})$—, $R^{10}C(O)$—, CON$(R^{10})_2$—, —$N(R^{10})_2$, or $R^{11}OC(O)NR^{10}$—,
c) aryl, heterocycle, cycloalkyl, alkenyl, $R^{10}O$—, $R^{11}S(O)_m$—, $R^{10}C(O)NR^{10}$—, CN, NO$_2$, $(R^{10})_2N$—C$(NR^{10})$—, $R^{10}C(O)$—, CON$(R^{10})_2$—, N$_3$—$N(R^{10})_2$, or $R^{11}OC(O)NR^{10}$—, and
d) $C_1$–$C_6$ alkyl substituted with an unsubstituted or substituted group selected from aryl, heterocyclic and $C_3$–$C_{10}$ cycloalkyl;

$R^{4b}$ and $R^{7b}$ are hydrogen;

$R^{5a}$ is selected from:
a) substituted or unsubstituted $C_1$–$C_{10}$ alkyl, $C_2$–$C_{10}$ alkenyl, $C_3$–$C_{10}$ cycloalkyl, aryl or heterocyclic group,
  wherein the substituent is selected from F, Cl, Br, NO$_2$, $R^{10}O$—, $R^{11}S(O)_m$—, $R^{10}C(O)NR^{10}$—, $(R^{10})_2NC(O)$—, CN, $(R^{10})_2N$—$C(NR^{10})$—, $R^{10}C(O)$—, —CON$(R^{10})_2$, N$_3$, —$N(R^{10})_2$, $R^{11}OC(O)NR^{10}$— and $C_1$–$C_{20}$ alkyl, and
b) $C_1$–$C_6$ alkyl substituted with an unsubstituted or substituted group selected from aryl, heterocycle and $C_3$–$C_{10}$ cycloalkyl;

$R^{5b}$ is selected from:
a) hydrogen, and
b) $C_1$–$C_3$ alkyl;

$R^6$ is independently selected from hydrogen or $C_1$–$C_6$ alkyl;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $CON(R^{10})_2$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $CON(R^{10})_2$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $CON(R^{10})_2$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, $CON(R^{10})_2$—, —$N(R^{10})_2$, or $R^{11}OC(O)NR^{10}$—;

$R^{10}$ is independently selected from hydrogen, $C_1$–$C_6$ alkyl, benzyl and aryl;

$R^{11}$ is independently selected from $C_1$–$C_6$ alkyl and aryl;

Q is:

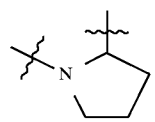

$A^1$ and $A^2$ are independently selected from: a bond, —CH=CH—, —C≡C—, —C(O)—, —C(O)NR$^{10}$—, O, —N(R$^{10}$)—, or $S(O)_m$;

V is selected from:
a) hydrogen,
b) aryl,
c) $C_1$–$C_{20}$ alkyl wherein from 0 to 4 carbon atoms are replaced with a heteroatom selected from O, S, and N, and
d) $C_2$–$C_{20}$ alkenyl, and
provided that V is not hydrogen if $A^1$ is $S(O)_m$ and V is not hydrogen if $A^1$ is a bond, n is 0 and $A^2$ is $S(O)_m$;

W is imidazolyl;

X, Y and Z are independently $H_2$ or O;

m is 0, 1 or 2;

n is 0, 1, 2, 3 or 4;

p is 0, 1, 2, 3 or 4;

r is 0 to 5, provided that r is 0 when V is hydrogen;

t is 3; and u is 1;

or the pharmaceutically acceptable salts, hydrates, crystal forms or isomers thereof.

2. A compound which inhibits Ras farnesyl-transferase having the Formula Ia:

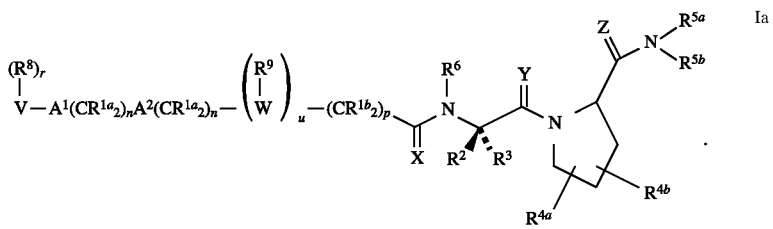

wherein: $R^{1a}$ and $R^{1b}$ are independently selected from:
a) hydrogen,
b) aryl, cycloalkyl, alkenyl, alkynyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, $N_3$, —$N(R^{10})_2$, or $R^{11}OC(O)NR^{10}$—, —$C(O)N(R^{10})_2$
c) $C_1$–$C_6$ alkyl unsubstituted or substituted by aryl, cycloalkyl, alkenyl, alkynyl, $R^{10}O$—, $R^{11}S(O)_m$—, $R^{10}C(O)NR^{10}$—, CN, $(R^{10})_2N$—$C(NR^{10})$—, $R^{10}C(O)$—, $N_3$, —$N(R^{10})_2$, or $R^{11}OC(O)$—$NR^{10}$—;

$R^2$ and $R^3$ are independently selected from:
a) a side chain of a naturally occurring amino acid,
b) an oxidized form of a side chain of a naturally occurring amino acid which is:
  i) methionine sulfoxide, or
  ii) methionine sulfone, and
c) substituted or unsubstituted $C_1$–$C_{20}$ alkyl, $C_2$–$C_{20}$ alkenyl, $C_3$–$C_{10}$ cycloalkyl or aryl,
  wherein the substituent is selected from F, Cl, Br, $N(R^{10})_2$, $NO_2$, $R^{10}O$—, $R^{11}S(O)_m$—, $R^{10}C(O)NR^{10}$—, CN, $(R^{10})_2N$—$C(NR^{10})$—, $R^{10}C(O)$—, $N_3$, —$N(R^{10})_2$, $R^{11}OC(O)NR^{10}$—, —$C(O)N(R^{10})_2$ and $C_1$–$C_{20}$ alkyl, and
d) $C_1$–$C_6$ alkyl substituted with an unsubstituted or substituted group selected from aryl and $C_3$–$C_{10}$ cycloalkyl;

or $R^2$ or $R^3$ are combined with $R^6$ to form a ring such that

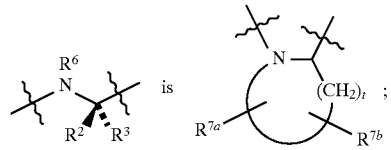

$R^{4a}$, $R^{4b}$, $R^{7a}$ and $R^{7b}$ are independently selected from:
a) hydrogen,
b) $C_1$–$C_6$ alkyl unsubstituted or substituted by alkenyl, $R^{10}O$—, $R^{11}S(O)_m$—, $R^{10}C(O)NR^{10}$—, CN, $N_3$, $(R^{10})_2N$—$C(NR^{10})$—, $R^{10}C(O)$—, —$C(O)N(R^{10})_2$, —$N(R^{10})_2$, or $R^{11}OC(O)NR^{10}$—,
c) aryl, cycloalkyl, alkenyl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, —$C(O)N(R^{10})_2$, $N_3$, —$N(R^{10})_2$, or $R^{11}OC(O)NR^{10}$—, and
d) $C_1$–$C_6$ alkyl substituted with an unsubstituted or substituted group selected from aryl and $C_3$–$C_{10}$ cycloalkyl;

R$^{5a}$ and R$^{5b}$ are independently selected from:
a) hydrogen,
b) substituted or unsubstituted C$_1$–C$_{20}$ alkyl, C$_2$–C$_{20}$ alkenyl, C$_3$–C$_{10}$ cycloalkyl or aryl,
   wherein the substituent is selected from F, Cl, Br, (R$^{10}$)$_2$NC(O)—, NO$_2$, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, —CON(R$^{10}$)$_2$, N$_3$, —N(R$^{10}$)$_2$, R$^{11}$OC(O)NR$^{10}$— and C$_1$–C$_{20}$ alkyl,
d) C$_1$–C$_6$ alkyl substituted with an unsubstituted or substituted group selected from aryl and C$_3$–C$_{10}$ cycloalkyl; or R$^{5a}$ and R$^{5b}$ are combined to form —(CH$_2$)$^s$—wherein one of the carbon atoms is optionally replaced by a moiety selected from: O, S(O)$_m$, —NC(O)—, and —N(COR$^{10}$)—;

R$^6$ is independently selected from hydrogen or C$_1$–C$_6$ alkyl;

R$^8$ is independently selected from:
a) hydrogen,
b) aryl, cycloalkyl, alkenyl, alkynyl, perfluoroalkyl, F, Cl, Br, R$^{10}$O—, R$^{11}$S(O)$_m$—, R$^{10}$C(O)NR$^{10}$—, CN, NO$_2$, R$^{10}$$_2$N—C(NR$^{10}$)—, R$^{10}$C(O)—, —C(O)N(R$^{10}$)$_2$, N$_3$, —N(R$^{10}$)$_2$, or R$^{11}$OC(O)NR$^{10}$—, and
c) C$_1$–C$_6$ alkyl unsubstituted or substituted by aryl, cycloalkyl, alkenyl, alkynyl, perfluoroalkyl, F, Cl, Br, R$^{10}$O—, R$^{11}$S(O)$_m$—, R$^{10}$C(O)NH—, CN, H$_2$N—C(NH)—, R$^{10}$C(O)—, N$_3$, —N(R$^{10}$)$_2$, or R$^{10}$OC(O)NH;

R$^9$ is selected from:
a) hydrogen,
b) alkenyl, alkynyl, perfluoroalkyl, F, Cl, Br, R$^{10}$O—, R$^{11}$S(O)$_m$—, R$^{10}$C(O)NR$^{10}$—, CN, NO$_2$, (R$^{10}$)$_2$N—C—(NR$^{10}$)—, R$^{10}$C(O)—, —C(O)N(R$^{10}$)$_2$, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, CN, (R$^{10}$)$_2$N—C(NR$^{10}$)—, R$^{10}$C(O)—, —C(O)N(R$^{10}$)$_2$, N$_3$, —N(R$^{10}$)$_2$, or R$^{11}$OC(O)NR$^{10}$—;

R$^{10}$ is independently selected from hydrogen, C$_1$–C$_6$ alkyl, benzyl and aryl;

R$^{11}$ is independently selected from C$_1$–C$_6$ alkyl and aryl;

A$^1$ and A$^2$ are independently selected from: a bond, —CH═CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) aryl,
c) C$_1$–C$_{20}$ alkyl wherein from 0 to 4 carbon atoms are replaced with a heteroatom selected from O, S, and N, and
d) C$_2$–C$_{20}$ alkenyl,
provided that V is not hydrogen if A$^1$ is S(O)$_m$ and V is not hydrogen if A$^1$ is a bond, n is 0 and A$^2$ is S(O)$_m$;

W is imidazolyl;

X, Y and Z are independently H$_2$ or O;

m is 0, 1 or 2;

n is 0, 1, 2, 3 or 4;

p is 0, 1, 2, 3 or 4;

r is 0 to 5, provided that r is 0 when V is hydrogen;

s is 4 or 5;

t is 3; and u is 1;

or a pharmaceutically acceptable salt, hydrate, crystal form or isomer thereof.

3. A compound which inhibits farnesyl-protein transferase which is:

N-[1-[1-(4-Cyanobenzyl)-1H-imidazol-5-ylacetyl] pyrrolidin-2(S)-ylmethyl]-3(S)-ethyl-proline N-(3-chlorophenylmethyl)-amide N-[1-[1-(4-Cyanobenzyl)-1H-imidazol-5-ylacetyl] pyrrolidin-2(S)-ylmethyl]-3(S)-ethyl-proline N-methyl-N-(3-chlorophenylmethyl)-amide N-[1-[1-(4-Cyanobenzyl)-1H-imidazol-5-ylacetyl]-3(S)-ethylpyrrolidin-2(S)-ylmethyl]-3(S)-ethyl-proline N-(3-chlorophenylmethyl)-amide N-[1-[1-(4-Cyanobenzyl)-1H-imidazol-5-ylacetyl]3(S)-ethylpyrrolidin-2(S)-ylmethyl]-3(S)-ethyl-proline N-methyl-N-(3-chlorophenylmethyl)-amide N-[1-(3-[1H-Imidazol-4-yl]propionyl)-pyrrolidin-2(S)-ylmethyl]-3(S)-ethyl-proline-N-methyl-N-(3-chlorophenylmethyl) amide N-[1-(3-[1H-Imidazol-4-yl]propionyl)-3(S)-ethylpyrrolidin-2(S)-ylmethyl]-3(S)-ethyl-proline-N-methyl-N-(3-chlorophenylmethyl) amide N-[1-(1-(1-Farnesyl)-1H-imidazol-5-ylacetyl)-pyrrolidin-2(S)-ylmethyl]-3(S)-ethyl-proline-N-methyl-N-(3-chlorophenylmethyl) amide N-[1-(1-(1-Geranyl)-1H-imidazol-5-ylacetyl)-pyrrolidin-2(S)-ylmethyl]-3(S)-ethyl-proline-N-methyl-N-(3-chlorophenylmethyl) amide N-[1-[1-(4-Methoxybenzyl)-1H-imidazol-5-ylacetyl] pyrrolidin-2(S)-ylmethyl]-3(S)-ethyl-proline-N-(3-chlorophenylmethyl) amide N-[1-[1-(4-Methoxybenzyl)-1H-imidazol-5-ylacetyl] pyrrolidin-2(S)-ylmethyl]-3(S)-ethyl-proline-N-methyl-N-(3-chlorophenylmethyl) amide N-[1-[1-(2-Naphthylmethyl)-1H-imidazol-5-ylacetyl] pyrrolidin-2(S)-ylmethyl]-3(S)-ethyl-proline-N-(3-chlorophenylmethyl) amide N-[1-[1-(2-Naphthylmethyl)-1H-imidazol-5-ylacetyl] pyrrolidin-2(S)-ylmethyl]-3(S)-ethyl-proline-N-methyl-N-(3-chlorophenylmethyl) amide or the pharmaceutically acceptable salts, hydrates, crystal forms or isomers thereof.

4. The compound according to claim 3 which inhibits farnesyl-protein transferase which is:

N-[1-(3-[1H-Imidazol-4-yl]propionyl)-pyrrolidin-2(S)-ylmethyl]-3(S)-ethyl-proline-N-methyl-N-(3-chlorophenylmethyl) amide

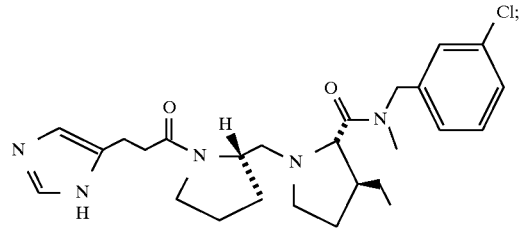

N-[1-[1-(4-Cyanobenzyl)-1H-imidazol-5-ylacetyl] pyrrolidin-2(S)-ylmethyl]-3(S)-ethyl-proline N-(3-chlorophenylmethyl)-amide

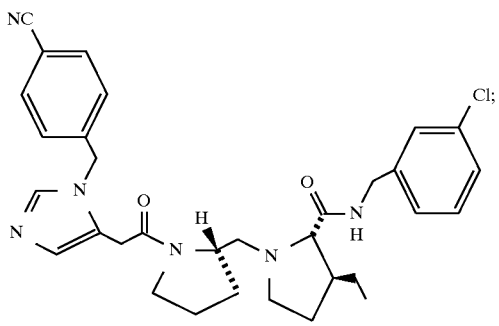

N-[1-[1-(4-Cyanobenzyl)-1H-imidazol-5-ylacetyl]
pyrrolidin-2(S)-ylmethyl]-3(S)-ethyl-proline
N-methyl-N-(3-chlorophenylmethyl)-amide

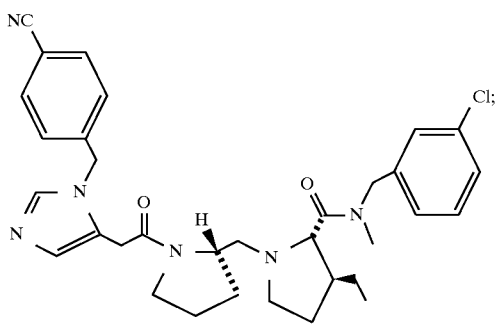

or a pharmaceutically acceptable salt, hydrates, crystal forms or optical isomer thereof.

5. The compound according to claim 3 which inhibits farnesyl-protein transferase which is:

N-[1-(3-[1H-Imidazol-4-yl]propionyl)-pyrrolidin-2(S)-ylmethyl]-3(S)-ethyl-proline-N-methyl-N-(3-chlorophenylmethyl) amide

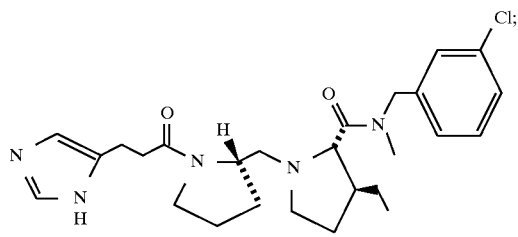

or a pharmaceutically acceptable salt, hydrates, crystal forms or optical isomer thereof.

6. The compound according to claim 3 which inhibits farnesyl-protein transferase which is:

N-[1-[1-(4-Cyanobenzyl)-1H-imidazol-5-ylacetyl]
pyrrolidin-2(S)-ylmethyl]-3(S)-ethyl-proline N-(3-chlorophenylmethyl)-amide

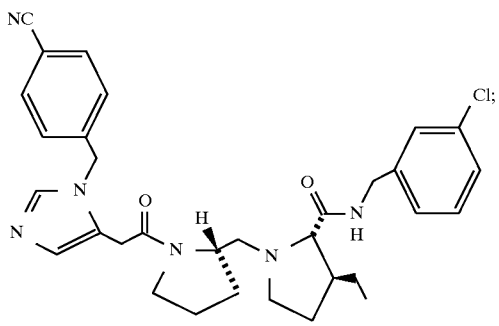

or a pharmaceutically acceptable salt, hydrates, crystal forms or optical isomer thereof.

7. The compound according to claim 3 which inhibits farnesyl-protein transferase which is:

N-[1-[1-(4-Cyanobenzyl)-1H-imidazol-5-ylacetyl]
pyrrolidin-2(S)-ylmethyl]-3(S)-ethyl-proline
N-methyl-N-(3-chlorophenylmethyl)-amide

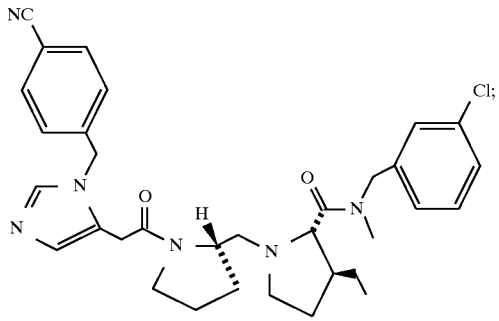

or a pharmaceutically acceptable salt, hydrates, crystal forms or optical isomer thereof.

8. A pharmaceutical composition comprising a pharmaceutical carrier, and dispersed therein, a therapeutically effective amount of a compound of claim 1.

9. A pharmaceutical composition comprising a pharmaceutical carrier, and dispersed therein, a therapeutically effective amount of a compound of claim 2.

10. A pharmaceutical composition comprising a pharmaceutical carrier, and dispersed therein, a therapeutically effective amount of a compound of claim 3.

11. A method for inhibiting farnesylation of Ras protein which comprises administering to a mammal in need thereof a therapeutically effective amount of the composition of claim 8.

12. A method for inhibiting farnesylation of Ras protein which comprises administering to a mammal in need thereof a therapeutically effective amount of the composition of claim 9.

13. A method for inhibiting farnesylation of Ras protein which comprises administering to a mammal in need thereof a therapeutically effective amount of the composition of claim 10.

14. A method for treating cancer which comprises administering to a mammal in need thereof a therapeutically effective amount of a composition of claim 8.

15. A method for treating cancer which comprises administering to a mammal in need thereof a therapeutically effective amount of a composition of claim 9.

16. A method for treating cancer which comprises administering to a mammal in need thereof a therapeutically effective amount of a composition of claim 10.

17. A method for treating neurofibromin benign proliferative disorder which comprises administering to a mammal in need thereof a therapeutically effective amount of a composition of claim 8.

18. A method for treating blindness related to retinal vascularization which comprises administering to a mammal in need thereof a therapeutically effective amount of a composition of claim 8.

19. A method for treating infections from hepatitis delta and related viruses which comprises administering to a mammal in need thereof a therapeutically effective amount of a composition of claim 8.

20. A method for preventing restenosis which comprises administering to a mammal in need thereof a therapeutically effective amount of a composition of claim 8.

21. A method for treating polycystic kidney disease which comprises administering to a mammal in need thereof a therapeutically effective amount of a composition of claim 8.

* * * * *